United States Patent
Okazawa et al.

(10) Patent No.: US 10,730,937 B2
(45) Date of Patent: Aug. 4, 2020

(54) ANTIBODIES AGAINST HMB1, AND COMPOSITION COMPRISING SAME FOR TREATING OR PREVENTING ALZHEIMER'S DISEASE

(71) Applicant: National University Corporation Tokyo Medical and Dental University, Tokyo (JP)

(72) Inventors: Hitoshi Okazawa, Tokyo (JP); Masunori Kajikawa, Nagoya (JP)

(73) Assignee: National University Corporation Tokyo Medical and Dental University, Bunkyo-ku, Tokyo (JP)

(*) Notice: Subject to any disclaimer, the term of this patent is extended or adjusted under 35 U.S.C. 154(b) by 0 days.

(21) Appl. No.: 16/324,192

(22) PCT Filed: Aug. 8, 2017

(86) PCT No.: PCT/JP2017/028773
§ 371 (c)(1),
(2) Date: Feb. 8, 2019

(87) PCT Pub. No.: WO2018/030405
PCT Pub. Date: Feb. 15, 2018

(65) Prior Publication Data
US 2019/0211092 A1    Jul. 11, 2019

Related U.S. Application Data

(60) Provisional application No. 62/372,472, filed on Aug. 9, 2016.

(51) Int. Cl.
| | |
|---|---|
| *C07K 16/24* | (2006.01) |
| *C12N 5/10* | (2006.01) |
| *A61K 39/00* | (2006.01) |
| *A61P 25/28* | (2006.01) |
| *C12N 5/16* | (2006.01) |
| *A61K 39/395* | (2006.01) |
| *C07K 16/18* | (2006.01) |
| *C12N 15/09* | (2006.01) |

(52) U.S. Cl.
CPC ............ *C07K 16/24* (2013.01); *A61K 39/395* (2013.01); *A61P 25/28* (2018.01); *C07K 16/18* (2013.01); *C12N 5/10* (2013.01); *C12N 5/16* (2013.01); *C12N 15/09* (2013.01); *A61K 2039/505* (2013.01); *C07K 2317/14* (2013.01)

(58) Field of Classification Search
CPC combination set(s) only.
See application file for complete search history.

(56) References Cited

U.S. PATENT DOCUMENTS

2011/0229487 A1    9/2011    Ando et al.

FOREIGN PATENT DOCUMENTS

| JP | 2004-107260 A | 4/2004 |
| JP | 2007-320919 A | 12/2007 |
| JP | 2008-520552 A | 6/2008 |
| WO | 2005/026209 A2 | 3/2005 |
| WO | 2008/099913 A1 | 8/2008 |

OTHER PUBLICATIONS

Kirkitadze et al., Acta Biochim Polonica, 52(2):417-423, (Year: 2005).*
Kyota Fujita, et al., "HMGB1, a pathogenic molecule that includes neurite degeneration via TLR4-MARCKS, is a potential therapeutic target for Alzheimer's disease", Scientific Reports, 2016, pp. 1-15.
Kazuyuki Takata, et al., "Role of high mobility group protein-1 (HMG1) in amyloid-β homeostasis", Biochemical and Biophysical Research Communications, 2003, pp. 699-703, vol. 301.
International Search Report for PCT/JP2017/028773 dated Sep. 12, 2017 [PCT/ISA/210].
International Preliminary Report on Patentability dated Sep. 12, 2017 [PCT/IPEA/409].
Communication, dated Apr. 14, 2019, issued by the International Bureau in PCT/JP2017/028773.
Communication, dated Mar. 19, 2020, issued by the European Patent Office in counterpart European Patent Application No. 17839475.5.

* cited by examiner

*Primary Examiner* — Kimberly Ballard
*Assistant Examiner* — Stacey N Macfarlane
(74) *Attorney, Agent, or Firm* — Sughrue Mion, PLLC

(57) ABSTRACT

An anti-HMGB1 antibody comprising a light chain variable region comprising complementarity-determining regions or the like including amino acid sequences of SEQ ID NOs: 4 to 6, and a heavy chain variable region comprising complementarity-determining regions or the like including amino acid sequences of SEQ ID NOs: 10 to 12, or an anti-HMGB1 antibody comprising a light chain variable region or the like comprising an amino acid sequence of SEQ ID NO: 3, and a heavy chain variable region comprising an amino acid sequence or the like of SEQ ID NO: 9, and a composition for treating or preventing Alzheimer's disease, comprising the same as an active ingredient.

8 Claims, 30 Drawing Sheets

Specification includes a Sequence Listing.

Fig. 3

Signal sequence

```
  1 ATGGTTTTCACACCTCAGATACTTGGACTTATGCTTTTTTGGATTTCAGCCTCCAGAGGT  60
    M  V  F  T  P  Q  I  L  G  L  M  L  F  W  I  S  A  S  R  G

61 GATATTGTGCTAACTCAGTCTCCAGCCACCCTGTCTGTGACTCCAGGAGATAGCGTCAGT 120
    D  I  V  L  T  Q  S  P  A  T  L  S  V  T  P  G  D  S  V  S

121 CTTTCCTGCAGGGCCAGCCAAAGTATTAGCAACAACCTACACTGGTATCAACAAAAATCA 180
    L  S  C  R  A  S  Q  S  I  S  N  N  L  H  W  Y  Q  Q  K  S

181 CATGAGTCTCCAAGGCTTCTCATCAAGTATGCTTCCAGTCCATCTCTGGAATCCCCTCC  240
    H  E  S  P  R  L  L  I  K  Y  A  S  Q  S  I  S  G  I  P  S

241 AGGTTCAGTGGCAGTGGATCAGGGACAGATTTCACTCTCAGTATCAACAGTGTGGAGACT 300
    R  F  S  G  S  G  S  G  T  D  F  T  L  S  I  N  S  V  E  T

301 GAAGATTTTGGAATGTATTTCTGTCAACAGACTAACAGCTGGCCGCTCACGTTCGGTGCT 360
    E  D  F  G  M  Y  F  C  Q  Q  T  N  S  W  P  L  T  F  G  A

361 GGGACCAAGCTGGAGCTGAAACGGGCTGATGCTGCACCAACTGTATCCATCTTCCCACCA 420
    G  T  K  L  E  L  K  R  A  D  A  A  P  T  V  S  I  F  P  P

421 TCCAGTGAGCAGTTAACATCTGGAGGTGCCCTCAGTCGTGTGCTTCTTGAACAACTTCTAC 480
    S  S  E  Q  L  T  S  G  G  A  S  V  V  C  F  L  N  N  F  Y

481 CCCAAAGACATCAATGTCAAGTGGAAGATTGATGGCAGTGAACGACAAAATGGCGTCCTG 540
    P  K  D  I  N  V  K  W  K  I  D  G  S  E  R  Q  N  G  V  L
```

Fig. 4

Signal sequence

```
  1  ATGACACTGACTCTAACCATGGGATGGAGCTGGATCTTTCTCTTCCTCCTGTCAGGAACT   60
     M  T  L  T  L  T  M  G  W  S  W  I  F  L  F  L  L  S  G  T

61  GCAGGTGTCCATTGCCAGGTCCAGCTGCAGCAGTCTGGACCTGAGCTGGTGAAGCCTGGA  120
     A  G  V  H  C  Q  V  Q  L  Q  Q  S  G  P  E  L  V  K  P  G

121  GCTTCAGTGAAGCTGTCCTGCAAGGCTTCTGGCTACACCTTCACTGACTATACTATACAC  180
     A  S  V  K  L  S  C  K  A  S  G  Y  T  F  T  D  Y  T  I  H

181  TGGGTGAAGCAGAGTCCTGGACAGGGACTTGAGTGGATTGGATGGATTTATCCTGGAAGT  240
     W  V  K  Q  S  P  G  Q  G  L  E  W  I  G  W  I  Y  P  G  S

241  GGTAATACTAAGTACAATGACAAGTTCAAGGGCAAGGCCACAATGACTGCAGACAAATCC  300
     G  N  T  K  Y  N  D  K  F  K  G  K  A  T  M  T  A  D  K  S

301  TCCAGCACAGCCTACATGCAGCTCAGCAGCCTGACCTCTGAGGATTCTGCGGTCTATTTC  360
     S  S  T  A  Y  M  Q  L  S  S  L  T  S  E  D  S  A  V  Y  F

361  TGTGCAAGAGGGTTTGCTTATTGGGGCCAAGGGACTCTGGTCACTGTCTCTGCAGCCAAA  420
     C  A  R  G  F  A  Y  W  G  Q  G  T  L  V  T  V  S  A  A  K

421  ACAACAGCCCCATCGGTCTATCCACTGGCCCCTGTGTGTGGAGATACAAGTGGCTCCTCG  480
     T  T  A  P  S  V  Y  P  L  A  P  V  C  G  D  T  S  G  S  S

481  GTGACTCTAGGATGCCTGGTCAAGGGTTATTTCCCTGAGCCAGTGACCTTGACCTGGAAC  540
     V  T  L  G  C  L  V  K  G  Y  F  P  E  P  V  T  L  T  W  N
```

ANTIBODIES AGAINST HMB1, AND COMPOSITION COMPRISING SAME FOR TREATING OR PREVENTING ALZHEIMER'S DISEASE

This application is a National Stage of International Application No. PCT/JP2017/028773 filed Aug. 8, 2017, claiming priority based on U.S. Patent Application No. 62/372,472 filed Aug. 9, 2016.

TECHNICAL FIELD

The present invention relates to an antibody against HMGB1, and a composition for treating or preventing Alzheimer's disease, comprising the same.

BACKGROUND ART

Alzheimer's disease (Alzheimer's-type dementia, AD) is a progressive neurodegenerative disease that occurs in the presenium and the senium. The major symptoms of Alzheimer's disease include memory disturbance, cognitive impairment, higher brain dysfunction (aphasia, apraxia, agnosia, and constructional apraxia), personality change, and the like. Because of such symptoms, Alzheimer's disease does not only degrade the quality of life of the patient him/herself but also seriously affects the lives of people around the patient such as his/her family. Moreover, the number of patients is steadily increasing along with the aging of the population. Hence, Alzheimer's disease has become a grave problem of the modern society worldwide.

For this reason, Alzheimer's disease has been energetically studied, and it has been revealed that, for example, Alzheimer's disease is neuropathologically characterized also by the deposition of senile plaques and the deposition of the neurofibrillary tangles (the entanglement of neurofibrills and paired helical filament (PHF)). It is considered that the deposition of these structures causes neurologic dysfunction and neuronal cell death (deficit of neurons) involved in the above-described symptoms.

In addition, it has been revealed that the senile plaques are structures generated by polypeptides having approximately 40 amino acids, which are referred to as amyloid β (Aβ), aggregating and being deposited outside neurons in a high density. Moreover, the neurofibrillary tangles have also been revealed to be structures generated by tau, which is a microtubule-associated protein, being phosphorylated to be dissociated from microtubules, which form the cytoskeletons, and being polymerized together.

As described above, regarding the pathogenesis and pathogenic mechanism of Alzheimer's disease, a mechanism considered as being most likely is that Aβ is aggregated (amyloid lesion) and this aggregation promotes the phosphorylation and polymerization of tau (tau lesion), eventually leading to the neuronal cell death (amyloid cascade hypothesis); however, the pathogenic mechanism and so on of Alzheimer's disease have not been found out yet. For this reason, the current situation is that no useful target molecules have been discovered in the development of a method for treating this disease.

By the way, as one of the non-histone chromatin-associated proteins involved in the structural maintenance and transcriptional regulation of DNA, an HMGB1 (High Mobility Group Box 1) protein is known. In addition, this HMGB1 has recently attracted attention not only for such an intranuclear function but also for its functioning as so-called DAMPs (damage-associated molecular patterns) when HMGB1 is released out of a cell due to the necrosis of the cell or is actively secreted out of a cell in vascular inflammatory signal response. Moreover, HMGB1 has also been reported to suppress phagocytosis by microglia. Since the aggregation of Aβ is removed by this phagocytosis, it has been suggested that HMGB1 is involved in lesions of Alzheimer's disease and the like (PTLs 1 and 2). However, as described above, the current situation is that Alzheimer's disease has not been understood yet including its pathogenic mechanism, and its curative agent has not been available yet.

CITATION LIST

Patent Literature

[PTL 1] Japanese Unexamined Patent Application Publication No. 2004-107260
[PTL 2] International Publication No. 2008/099913

SUMMARY OF INVENTION

Technical Problem

The present invention has been made in view of the above-described problems of the conventional techniques, and an object thereof is to provide a substance that makes it possible to treat or prevent Alzheimer's disease.

Solution to Problem

The present inventors have earnestly studied to achieve the above object. As a result, the present inventors have successfully obtained a mouse monoclonal antibody that exhibits a high affinity for the HMGB1 protein. In addition, the present inventors have found that administering the antibody to Alzheimer's disease model mice recovers the cognitive impairment, the abnormal spine morphology, and the DNA damage of the mice. Moreover, the present inventors have also determined the light chain variable region and the heavy chain variable region of the antibody as well as sequences of complementarity-determining regions (CDR) 1 to 3 of each region. These findings have led to the completion of the present invention.

Specifically, the present invention relates to an antibody against HMGB1, and a composition for treating or preventing Alzheimer's disease, comprising the same, and more specifically provides the following:

<1> A monoclonal antibody against HMGB1, the antibody having any one of the following features (a) and (b):
  (a) comprising
    a light chain variable region comprising complementarity-determining regions including amino acid sequences of SEQ ID NOs: 4 to 6 or complementarity-determining regions including the amino acid sequences in at least any one of which one or more amino acids are substituted, deleted, added, and/or inserted, and
    a heavy chain variable region comprising complementarity-determining regions including amino acid sequences of SEQ ID NOs: 10 to 12 or complementarity-determining regions including the amino acid sequences in at least anyone of which one or more amino acids are substituted, deleted, added, and/or inserted; and
  (b) comprising
    a light chain variable region comprising an amino acid sequence of SEQ ID NO: 3 or the amino acid sequence in at least any portion of which one or more amino acids are substituted, deleted, added, and/or inserted, and a heavy chain variable region comprising an amino acid sequence of SEQ ID NO: 9 or the amino acid sequence in at least any portion of which one or more amino acids are substituted, deleted, added, and/or inserted.

<2> A composition for treating or preventing Alzheimer's disease, comprising the antibody according to <1> as an active ingredient.
<3> A DNA encoding the antibody according to <1>.
<4> A vector comprising the DNA according to <3>.
<5> A host cell producing the antibody according to <1> or comprising the DNA according to <3> or the vector according to <4>.
<6> A hybridoma producing the antibody according to <1>.

Advantageous Effects of Invention

According to the present invention, it is possible to provide an antibody that exhibits a high affinity for HMGB1 protein. According to the present invention, it is also possible to provide a drug and a method that use the antibody and are effective for treating or preventing Alzheimer's disease.

BRIEF DESCRIPTION OF DRAWINGS

FIG. 3 is a diagram showing sequences of the light chain (mouse Igk/signal sequence, part of the variable region and the constant region) of the anti-HMGB1 monoclonal antibody (2C8C). Note that the DNA sequence and the amino acid sequence in the diagram are shown in SEQ ID NOs: 1 and 2.

FIG. 4 is a diagram showing sequences of the heavy chain (mouse IgG2a/signal sequence, part of the variable region and the constant region) of the anti-HMGB1 monoclonal antibody (2C8C). Note that the DNA sequence and the amino acid sequence are shown in SEQ ID NOs: 7 and 8. In addition, in the following figures, the anti-HMGB1 antibody or anti-HMGB means the anti-HMGB1 monoclonal antibody (2C8C) unless otherwise specified as a rabbit-derived polyclonal antibody.

As shown in FIGS. 5G and H, the accumulation of DNA damage with aging was observed particularly in the 5×FAD mice.

As shown in FIGS. 5I and J, the subcutaneous injection of the anti-HMGB1 antibody completely recovered the DNA damage in the 5×FAD mice.

As shown in FIG. 7A and FIG. 7B, when $Aβ_{1-42}$ was incubated for 48 hours in the presence or absence of HMGB1 or in the presence or absence of HMGB1 antibody, HMGB1 significantly reduced fibrils/aggregates of Aβ and increased the other types of Aβ species (monomers, oligomers, ADDLs/protofibrils, and the like). Moreover, the addition of the anti-HMGB1 antibody suppressed the decrease of fibrils/aggregates of Aβ by HMGB1 and inhibited the increase of oligomers and ADDLs/protofibrils of Aβ by HMGB1.

In FIG. 7D, the result of determination from these molecular weights indicates Aβ inhibited the HMGB1 polymerization and generated another type (heteromers of Aβ and HMGB1).

As shown in FIG. 8E and FIG. 8F, the addition of the anti-HMGB1 antibody enhanced the phagocytosis of TAMRA-Aβ (see the photograph in the middle of FIG. 8E).

DESCRIPTION OF EMBODIMENTS

<Antibody Against HMGB1 Protein>

Figure 1A:
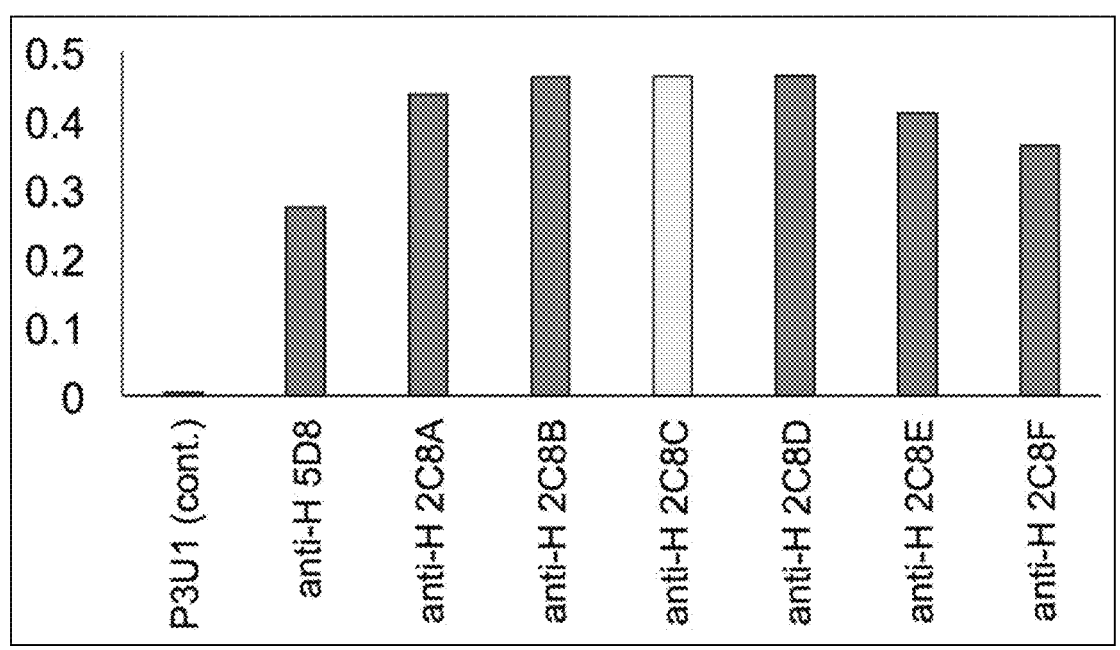
FIG. 1A is a graph showing the result of comparing 7 clones of an anti-HMGB1 antibody in terms of affinity for HMGB1 by ELISA using a GST-fusion HMGB1 protein. In the figure, the vertical axis shows absorbance (O.D.) in a wavelength of 450 to 630 nm.

As shown in Examples, which are described later, the present inventors have successfully obtained a mouse monoclonal antibody (hereinafter also referred to as a "2C8C antibody") that exhibits a high affinity for the HMGB1 protein. The present inventors have also found for example that administering the antibody to an Alzheimer's disease model mouse recovers the cognitive impairment, the abnormal spine morphology, and the DNA damage in the mouse. Moreover, the present inventors have also determined the sequences of the light chain variable region and the heavy chain variable region as well as the complementarity-determining regions (CDR) 1 to 3 in the regions of the antibody.

The present invention provides a monoclonal antibody against HMGB1, based on such matters, that has the characteristics described in (a) or (b) below.

(a) comprising
   a light chain variable region comprising complementarity-determining regions including amino acid sequences of SEQ ID NOs: 4 to 6 or complementarity-determining regions including the amino acid sequences in at least any one of which one or more amino acids are substituted, deleted, added, and/or inserted, and
   a heavy chain variable region comprising complementarity-determining regions including amino acid sequences of SEQ ID NOs: 10 to 12 or complementarity-determining regions including the amino acid sequences in at least anyone of which one or more amino acids are substituted, deleted, added, and/or inserted (b) comprising
   a light chain variable region comprising an amino acid sequence of SEQ ID NO: 3 or the amino acid sequence in at least any portion of which one or more amino acids are substituted, deleted, added, and/or inserted, and
   a heavy chain variable region comprising an amino acid sequence of SEQ ID NO: 9 or the amino acid sequence in at least any portion of which one or more amino acids are substituted, deleted, added, and/or inserted.

Note that the amino acid sequences of SEQ ID NOs: 4 to 6 represent the amino acid sequences of the light chain CDR1 to CDR3 of the 2C8C antibody, and the amino acid sequences of SEQ ID NOs: 10 to 12 represent the amino acid sequences of the heavy chain CDR1 to CDR3 of the 2C8C antibody. In addition, the amino acid sequence of SEQ ID NO: 3 represents the amino acid sequence of the light chain variable region of the 2C8C antibody, and the amino acid sequence of SEQ ID NO: 9 represents the amino acid sequence of the heavy chain variable region of the 2C8C antibody.

In the present invention, the "HMGB1 (High Mobility Group Box 1)" refers to a protein which is also referred to as HMG1, HMG3, SBP-1, and HMG-1. If derived from human, the protein is a protein including an amino acid sequence identified by NCBI reference sequence: NP_002119.1 (a protein is encoded by a nucleotide sequence identified by NCBI reference sequence: NM_002128.5). Nevertheless, the DNA sequence of a gene is mutated naturally (i.e., non-artificially) by a mutation or the like, and the amino acid sequence of a protein encoded by the gene is also modified accordingly. Thus, the "HMGB1" according to the present invention is not limited to the protein having the typical amino acid sequence, and also includes such naturally-occurring mutants. In addition, the sequence of the HMGB1 is known to be extremely highly conserved, and the human-derived HMGB1 and a rat-derived one, for example, completely coincide with each other except that 2 amino acids are different in the C-terminal positively/negatively charged region.

In the present invention, the "antibody" includes all classes and subclasses of immunoglobulins. The "antibody" includes a polyclonal antibody and a monoclonal antibody, and also means to include the form of a functional fragment of an antibody. A "polyclonal antibody" is an antibody preparation containing different antibodies against different epitopes. Meanwhile, a "monoclonal antibody" means an antibody (including an antibody fragment) obtained from a substantially uniform antibody population. In contrast to a polyclonal antibody, a monoclonal antibody recognizes a single determinant on an antigen. The antibody of the present invention is preferably a monoclonal antibody. The antibody of the present invention is an antibody separated and/or recovered (i.e., isolated) from components in a natural environment.

The origin, type, shape, and so forth of the antibody of the present invention are not particularly limited, as long as the antibody can bind to the above-described HMGB1 protein. Concretely, the antibody of the present invention includes an antibody derived from a non-human animal (for example, mouse antibody, rat antibody, camel antibody), a human-derived antibody, a chimeric antibody, a humanized antibody, and functional fragments of these antibodies. In a case where the antibody of the present invention is administered as a pharmaceutical drug to a human, a chimeric antibody or a humanized antibody is desirable from the viewpoint of side effect reduction.

In the present invention, a "chimeric antibody" is an antibody obtained by linking a variable region of an antibody of one species to a constant region of an antibody of another species. A chimeric antibody can be obtained as follows, for example. Specifically, a mouse is immunized with an antigen. A portion corresponding to an antibody variable part (variable region) which binds to the antigen is cut out from a gene of a monoclonal antibody of the mouse. The portion is linked to a gene of a constant part (constant region) of an antibody derived from human bone marrow. This is incorporated into an expression vector, which is then introduced into a host for the production of a chimeric antibody (for example, Japanese Unexamined Patent Application Publication No. Hei 8-280387, U.S. Pat. Nos. 4,816, 397, 4,816,567, 5,807,715).

As the constant region of the chimeric antibody, normally, those of human-derived antibodies are used. For example, Cγ1, Cγ2, Cγ3, Cγ4, Cμ, Cδ, Cα1, Cα2, and Cε can be used as the constant region of the heavy chain. Moreover, Cκ and Cλ can be used as the constant region of the light chain. The amino acid sequences of these constant regions and the base sequences encoding these amino acid sequences are known. In addition, to improve the stability of the antibody itself or the stability of the antibody production, one or more amino acids in the constant regions of the human-derived antibodies may be substituted, deleted, added, and/or inserted.

In the present invention, a "humanized antibody" is an antibody obtained by grafting (CDR grafting) a gene sequence of an antigen-binding site (CDR) of a non-human (such as mouse)-derived antibody onto a human-derived antibody gene. The preparation methods such as overlap extension PCR are known (for example, European Patent Application Publication No. 239400, European Patent Application Publication No. 125023, International Publication No. WO90/07861, International Publication No. WO96/02576). A variable region of an antibody is normally composed of three CDRs flanked by four FRs. CDRs are regions substantially determining the binding specificity of an antibody. While the amino acid sequences of CDRs are rich in diversity, the amino acid sequences of FRs often show a high homology even among antibodies having different binding specificities. For this reason, generally it is said that grafting CDRs enables transfer of the binding specificity of a certain antibody to another antibody. Moreover, from the viewpoint of maintaining the function of a CDR, in grafting a non-human-derived CDR onto a human FR, a human FR having a high homology with a FR derived from the non-human animal is selected. In other words, since amino acids in a CDR not only recognize an antigen, but also coordinate with amino acids of FRs next to the CDR, and are also involved in the maintenance of the loop structure of the CDR, it is preferable to utilize a human FR whose amino acid sequence has a high homology with the amino acid sequence of a FR adjacent to the CDR to be grafted.

Known human FRs having a high homology with FRs derived from non-human animals can be searched, for example, by utilizing an antibody-dedicated search system (http://www.bioinf.org.uk/abysis/) available in the Internet. To match with the sequence of a human FR thus obtained, a mutation can be introduced into the sequence of a non-human-derived antibody other than those of CDRs. Alternatively, if a gene (cDNA) encoding the amino acid sequence of a human FR obtained by searching is available, a non-human-derived CDR may be introduced into the sequence. A mutation can be introduced, for example, by using techniques known in the art, such as nucleic acid synthesis, site-directed mutagenesis, and so forth.

The affinity of a humanized antibody thus prepared to an antigen is qualitatively or quantitatively measured and evaluated, so that FRs of a human-derived antibody can be suitably selected which enables CDRs to form a favorable antigen-binding site when the FRs ligated to each other with the CDRs in between. Additionally, as necessary, according to a method described in Sato, K. et al., Cancer Res, 1993, 53, 851-856 or the like, amino acid residues of FRs can also be substituted so that CDRs of the humanized antibody can form an appropriate antigen-binding site. Further, the affinity of the amino acid-substituted mutant antibody to an antigen is measured and evaluated, so that a mutated FR sequence having a desired characteristic can be selected.

In the present invention, a "functional fragment" of an antibody means apart (partial fragment) of the antibody, which specifically recognizes the HMGB1 protein. Concrete examples thereof include Fab, Fab', F(ab')2, a variable region fragment (Fv), a disulfide bonded Fv, a single chain Fv (scFv), a sc(Fv)2, a diabody, a polyspecific antibody, polymers thereof, and the like.

Here, "Fab" means a monovalent antigen-binding fragment of an immunoglobulin, composed of a part of one light chain and a part of one heavy chain. Fab can be obtained by papain digestion of an antibody or by a recombinant method. "Fab'" is different from Fab in that a small number of residues, including one or more cysteines in an antibody hinge region, are added to the carboxy terminus of a heavy chain CH1 domain. "F(ab')2" means a bivalent antigen-binding fragment of an immunoglobulin, composed of parts of two light chains and parts of two heavy chains.

A "variable region fragment (Fv)" is a smallest antibody fragment having complete antigen recognition and binding sites. An Fv is a dimer in which a heavy chain variable region and a light chain variable region are strongly linked by non-covalent bonding. A "single chain Fv (scFv)" includes a heavy chain variable region and a light chain variable region of an antibody, and these regions exist in a single polypeptide chain. A "sc (Fv) 2" is a single chain obtained by linking two heavy chain variable regions and two light chain variable regions with a linker or the like. A "diabody" is a small antibody fragment having two antigen-binding sites. This fragment includes a heavy chain variable region linked to a light chain variable region in a single polypeptide chain, and each region forms a pair with a complementary region of another chain. A "polyspecific antibody" is a monoclonal antibody having binding specificities to at least two different antigens. For example, a polyspecific antibody can be prepared by coexpression of two immunoglobulin heavy chain/light chain pairs in which the two heavy chains have different specificities.

The antibody of the present invention includes antibodies whose amino acid sequences are modified without impairing desirable activities (affinity for an antigen and/or other biological properties). Such an amino acid sequence mutant can be prepared, for example, by introduction of a mutation into a DNA encoding an antibody chain of the 2C8C antibody, or by peptide synthesis. Examples of such a modification include substitution, deletion, addition, and/or insertion of residues in the amino acid sequence of the antibody. A site where the amino acid sequence of the antibody is modified may be a constant region of a heavy chain or a light chain of the antibody or a variable region (FR and CDR) thereof, as long as the resulting antibody has activities equivalent to those before the modification. It is conceivable that a modification on an amino acid other than those in CDR has a relatively small influence on the binding affinity for an antigen. As of now, there are known screening methods for antibodies whose affinity for an antigen has been enhanced by modifying an amino acid of CDR (PNAS, 102: 8466-8471 (2005), Protein Engineering, Design & Selection, 21: 485-493 (2008), International Publication No. WO2002/051870, J. Biol. Chem., 280: 24880-24887 (2005), Protein Engineering, Design & Selection, 21:345-351 (2008), MAbs. March-April; 6 (2):437-45 (2014)). Additionally, now, an antibody whose affinity for an antigen has been enhanced can also be modeled by utilizing an integrated computing chemical system or the like (for example, Molecular Operating Environment manufactured by CCG ULC in Canada) (see, for example, http://www.rsi.co.jp/kagaku/cs/ccg/products/application/protein.html). Further, as described in Protein Eng Des Sel. 2010 August; 23 (8):643-51, a case has been known where CDR1 in the heavy chain variable region and CDR3 in the light chain variable region are not involved in the affinity for an antigen. Moreover, similarly, Molecular Immunology 44: 1075-1084 (2007)) has reported that, in most antibodies, CDR2 in the light chain variable region is not involved in the affinity for an antigen. As described above, regarding the affinity of the antibody for an antigen, equivalent activities can be exhibited without requiring all of CDRs 1 to 3 in each heavy chain variable region and light chain variable region. Actually, Biochem Biophys Res Commun. 2003 Jul. 18; 307 (1):198-205, J Mol Biol. 2004 Jul. 9; 340 (3):525-42, and J Mol Biol. 2003 Aug. 29; 331 (5):1109-20 have reported cases where having at least one CDR of the original antibody maintains the affinity for an antigen. Thus, the antibody of the present invention also includes an antibody comprising at least one CDR of the 2C8C antibody.

Moreover, the number of amino acids modified in the antibody of the present invention is preferably 10 amino acids or less, more preferably 5 amino acids or less, and most preferably 3 amino acids or less (for example, 2 amino acids or less, 1 amino acid). The amino acid modification is preferably conservative substitution. In the present invention, the "conservative substitution" means substitution with a different amino acid residue having a chemically similar side chain. Groups of amino acid residues having chemically similar amino acid side chains are well known in the technical field to which the present invention pertains. For example, amino acids can be grouped into acidic amino acids (aspartic acid and glutamic acid), basic amino acids (lysine, arginine, histidine), and neutral amino acids such as amino acids having a hydrocarbon chain (glycine, alanine, valine, leucine, isoleucine, proline), amino acids having a hydroxy group (serine, threonine), sulfur-containing amino acids (cysteine, methionine), amino acids having an amide group (asparagine, glutamine), an amino acid having an imino group (proline), and amino acids having an aromatic group (phenylalanine, tyrosine, tryptophan).

In addition, the antibody of the present invention also includes an antibody wherein the amino acid sequence after modification has an antibody chain whose amino acid sequence has a homology of 80% or more at the amino acid sequence level with the antibody chain of the 2C8C antibody, as long as the antibody has activities equivalent to those before the modification. The homology should be at least 80%, preferably 85% or more, more preferably 90% or more, and further preferably 95% or more (for example, 96% or more, 97% or more, 98% or more, 99% or more). Moreover, the sequence homology can be determined by utilizing the BLASTP (amino acid level) program (Altschul et al. J. Mol. Biol., 215:403-410, 1990). This program is based on the algorithm BLAST of Karlin and Altschul (Proc. Natl. Acad. Sci. USA, 87:2264-2268, 1990, Proc. Natl. Acad. Sci. USA, 90:5873-5877, 1993). When an amino acid sequence is analyzed by BLASTP, the parameters are set to, for example, score=50, word length=3. Meanwhile, when an amino acid sequence is analyzed by using the Gapped BLAST program, the analysis can be conducted as described in Altschul et al. (Nucleic Acids Res. 25:3389-3402, 1997). When the BLAST and Gapped BLAST programs are used, the default parameters of each program are used. The specific procedures of these analysis methods are known. Note that in the present Specification, the "homology" includes "identity".

Moreover, "having equivalent activities" means that the affinity for an antigen, or the like is equivalent to (for example, 70% or more, preferably 80% or more, more preferably 90% or more of) those of a target antibody (typically, the 2C8C antibody). Furthermore, as shown in Examples described below, those skilled in the art can evaluate the affinity for an antigen as appropriate by using a known immunological approach (for example, ELISA (enzyme-linked immunosorbent assay) and SPR (surface plasmon resonance)).

Further, the modification on the antibody of the present invention may be a modification on post-translational process of the antibody, for example, the change in the number of sites of glycosylation or in location of the glycosylation. Thereby, for example, the ADCC activity (antibody-dependent cellular cytotoxicity) of the antibody can be improved. Glycosylation of the antibody is typically N-linked or O-linked glycosylation. The glycosylation of the antibody greatly depends on host cells used for expression of the antibody. The glycosylation pattern can be modified by known methods such as introduction or deletion of a certain enzyme involved in carbohydrate production (Japanese Unexamined Patent Application Publication No. 2008-113663, U.S. Pat. Nos. 5,047,335, 5,510,261, 5,278,299, International Publication No. WO99/54342). Further, in the present invention, for the purpose of increasing the stability of the antibody or other purposes, an amino acid subjected to deamidation or an amino acid adjacent to the amino acid subjected to the deamidation may be substituted with a different amino acid to suppress the deamidation. Moreover, the stability of the antibody can also be increased by substituting glutamic acid with a different amino acid. The present invention also provides an antibody thus stabilized.

As described later in Examples, the antibody of the present invention can be prepared by a hybridoma method, or can be prepared by a recombinant DNA method. The hybridoma method is typically a method by Kohler and Milstein (Kohler & Milstein, Nature, 256: 495 (1975)). In this method, antibody-producing cells used in the cell fusion process are spleen cells, lymph node cells, peripheral blood leucocytes, or the like of an animal (for example, mouse, rat, hamster, rabbit, monkey, goat) immunized with an antigen (the HMGB1 protein, a partial peptide thereof, a protein in which an Fc protein or the like is fused to the protein or peptide, cells expressing these, or the like). It is also possible to use antibody-producing cells which are obtained by treating, with the antigen in a medium, the above-described cells, lymphocytes, or the like having been isolated from a non-immunized animal in advance. As myeloma cells, various known cell lines can be used. The antibody-producing cells and the myeloma cells may be originated from different animal species, as long as they can be fused. However, the antibody-producing cells and the myeloma cells are preferably originated from the same animal species. Hybridomas can be produced, for example, by cell fusion between mouse myeloma cells and spleen cells obtained from a mouse immunized with the antigen. By the subsequent screening, a hybridoma which produces a monoclonal antibody specific to the HMGB1 protein can be obtained. The monoclonal antibody against the HMGB1 protein can be obtained by culturing the hybridoma, or from the ascitic fluid of a mammal having been subjected to the hybridoma administration.

The recombinant DNA method is a method by which the antibody of the present invention is produced as a recombinant antibody as follows. A DNA encoding the antibody of the present invention is cloned from a hybridoma, B cells, or the like. The cloned DNA is incorporated into an appropriate vector, which is introduced into host cells (for example, a mammalian cell line such as HEK cells, *Escherichia coli*, yeast cells, insect cells, plant cells, or the like) for the production (for example, P. J. Delves, Antibody Production: Essential Techniques, 1997 WILEY, P. Shepherd and C. Dean Monoclonal Antibodies, 2000 OXFORD UNIVERSITY PRESS, Vandamme A. M. et al., Eur. J. Biochem. 192: 767-775 (1990)). For the expression of the DNA encoding the antibody of the present invention, DNAs encoding a heavy chain and a light chain may be incorporated separately into expression vectors to transform the host cells. Alternatively, the DNAs encoding a heavy chain and a light chain may be incorporated into a single expression vector to transform the host cells (see International Publication No. WO94/11523). The antibody of the present invention can be obtained in a substantially pure and homogeneous form by culturing the host cells, followed by separation and purification of the host cells or the culture liquid. For the separation and purification of the antibody, a normal method used for polypeptide purification can be employed. Once a transgenic animal (bovine, goat, sheep, pig, or the like) incorporating the antibody gene is prepared by using a transgenic animal preparation technique, a large amount of the monoclonal antibody derived from the antibody gene can also be obtained from milk of the transgenic animal.

The present invention can also provide: the DNA encoding the antibody of the present invention; a vector comprising the DNA; host cells comprising the DNA; and a method for producing the antibody, comprising culturing the host cells and recovering the antibody.

<Composition Comprising Antibody against HMGB1, etc>

As described in Examples below, the antibody of the present invention exhibits a high affinity for the HMGB1 protein and recovers cognitive impairment and the like in an Alzheimer's disease model mouse. Accordingly, the antibody of the present invention can be utilized to treat or prevent Alzheimer's disease. Thus, the present invention also provides a pharmaceutical composition comprising the antibody of the present invention as an active ingredient and a Method for treating or preventing Alzheimer's disease, comprising a step of administering a therapeutically and prophylactically effective amount of the antibody of the present invention to a mammal including a human.

In the present invention, "Alzheimer's disease" is a neurodegenerative disease which is also referred to as Alzheimer's-type dementia or AD and includes "familial Alzheimer's disease" and "hereditary Alzheimer's disease" which are attributable to gene mutation and "sporadic Alzheimer's disease" which is caused by environmental factors such as lifestyle habit and stress. Moreover, "Alzheimer's disease" also not only includes stages at which clinical signs are observed including expression of symptoms such as memory disturbance, cognitive impairment, higher brain dysfunction (aphasia, apraxia, agnosia, constructional apraxia), and personality change and occurrence of brain atrophy, which is diagnosed using diagnostic imaging, but also includes the stage of mild cognition impairment (MCI), which is said to be the stage before that where the above symptoms are observed and preclinical Alzheimer's disease (preclinical AD) in which aggregation of amyloid β (Aβ) (amyloid lesion) has occurred although the cognitive function is normal, which is prior to the mild cognition impairment (MCI). In addition, the treatment of Alzheimer's disease includes not only recovery and amelioration of the lesions of Alzheimer's disease, including amyloid lesions, but also suppression of the progress of Alzheimer's disease.

The pharmaceutical composition comprising the antibody of the present invention as an active ingredient can be used in the form of a composition comprising the antibody of the present invention and any ingredient, for example, a saline, an aqueous solution of glucose, a phosphate buffer, or the like. The pharmaceutical composition of the present invention may be formulated in a liquid or lyophilized form as necessary, and may also optionally comprise a pharmaceutically acceptable carrier or medium, for example, a stabilizer, a preservative, an isotonic agent, or the like.

Examples of the pharmaceutically acceptable carrier include: mannitol, lactose, saccharose, human albumin, and the like for a lyophilized preparation; and a saline, water for injection, a phosphate buffer, aluminum hydroxide, and the like for a liquid preparation. However, the examples are not limited thereto.

The method for administering the pharmaceutical composition differs depending on the age, weight, sex, and health state of an administration target, and the like. The administration can be carried out by any administration route: oral administration and parenteral administration (for example, subcutaneous administration, intravenous administration, intraarterial administration, local administration). A preferable administration method is parenteral administration, more preferably subcutaneous administration. The dose of the pharmaceutical composition may vary depending on the age, weight, sex, and health state of a patient, the degree of the progression of the symptom, and ingredients of the pharmaceutical composition to be administered. Nevertheless, the dose is normally 0.1 to 1000 mg, preferably 1 to 100 mg, per kg body weight for an adult per day. The pharmaceutical composition of the present invention may be used in combination with a known pharmaceutical product used for the treatment of Alzheimer's disease.

Hereinabove, preferable embodiments (applications) of the antibody of the present invention have been described. However, the antibody of the present invention is not limited to the above-described embodiments. Since the antibody of the present invention has a high affinity for the HMGB1 protein, the antibody of the present invention can be favorably used, for example, for a reagent and a diagnostic agent for detecting the HMGB1 protein, a drug for use in a missile therapy targeting the HMGB1 protein, and a pharmaceutical composition for treating or preventing a disease associated with the HMGB1 protein.

When used for a reagent and a diagnostic agent for detecting the HMGB1 protein, a labeling substance may be directly or indirectly bound to the antibody of the present invention for the detection. Such a labeling substance includes a radioactive isotope, a fluorescent substance, and a luminescent substance.

When used for the drug for use in the missile therapy targeting the HMGB1 protein, a substance which needs to be delivered may be directly or indirectly bound to the antibody of the present invention. Such a substance includes, for example, cytotoxic substances such as a photosensitive substance, a toxic peptide, a chemotherapeutic agent, and a radioactive chemical substance.

In addition, in the present invention, the disease associated with the HMGB1 protein may be any disease for which the expression of the HMGB1 protein is involved in the onset and the progression and exacerbation of the symptom. Such a disease includes, for example, systemic amyloidosis and sepsis besides Alzheimer's disease.

EXAMPLES

Hereinafter, the present invention is described in more detail based on Examples; however, the present invention is not limited to the following Examples. In addition, the present Examples were carried out with materials and methods described below.

Mice

5×FAD transgenic mice (5×FAD mice), which were mice overexpressing the human APP (770) with mutations [Swedish (KM670/671NL), Florida (1716V), and London (V717I)] of the familial Alzheimer's disease (FAD) and the human PS1 with FAD mutations (M146L and L285V) were overexpressed, were purchased from The Jackson Laboratory (CA, USA). Note that in the transgenic mice, both APP and PS1 transgenes were expressed under the control of the mouse Thy1 promoter (see Oakley, H. et al., J. Neurosci., 2006, vol. 26, pp. 10129 to 10140). In addition, the genetic background of the transgenic mice was C57/B6XSJL, which was produced by crossbreeding C57/B6 female and SJL/J female mice.

Western Blot Analysis

The cerebral cortex tissues or the primary cultured cortical neurons of the mice were homogenized with a plastic homogenizer (product name: BioMasher II, manufactured by Nippi. Inc., Tokyo, Japan) after the addition of a lysis buffer (100 mM Tris-HCl (pH 7.5, manufactured by Sigma, Mo., USA), 2% SDS (manufactured by Sigma, Mo., USA), 1 mM DTT (manufactured by Sigma, MO, USA), and a protease inhibitor cocktail (manufactured by Calbiochem, catalog number: 539134, 1:200 dilution)). The protein lysates obtained were incubated at 4° C. for 30 minutes while being rotated, and were thereafter boiled at 100° C. for 15 minutes. The protein lysates were then subjected to a centrifugal treatment (16,000×g, 10 minutes, 4° C.). Supernatants were diluted with an equal volume of a sample buffer (125 mM Tris-HCl (pH 6.8, manufactured by Sigma, MO, USA), 4% SDS (manufactured by Sigma, Mo., USA), 20% glycerol (manufactured by Wako, Osaka, Japan), 12% mercaptoethanol (manufactured by Wako, Osaka, Japan), and 0.05% BPB (manufactured by Nacalai, Kyoto, Japan).

The samples thus prepared were separated by SDS-PAGE, transferred to Immobilon (Registered Trademark)-P polyvinylidene difluoride membranes (manufactured by Millipore, Mass., USA) through a semi-dry method, and blocked by 2% BSA (manufactured by Nacalai, Kyoto, Japan) or 5% milk in TBST (10 mM Tris-HCl, pH 8.0, 150 mM NaCl, 0.05% Tween-20).

In addition, primary antibodies and secondary antibodies shown below were diluted in TBST containing 0.2% BSA or an immunoreaction enhancer reagent (product name: Can Get Signal (Registered Trademark) solution, Osaka, Japan) for use.

<Primary Antibodies>

Mouse anti-actin antibody, 1:1000 dilution (catalog number: sc-8334, manufactured by Santa Cruz Biotechnology, Tex., USA), Rabbit anti-GFP antibody, 1:1000 dilution (catalog number: sc-47778, manufactured by Santa Cruz Biotechnology, Tex., USA), Mouse anti-GAPDH antibody, 1:3000 dilution (catalog number: MAB374, manufactured by Millipore, Mass., USA), Mouse anti-amyloid β antibody, 1:5000 dilution (clone 82E1, IBL, Gunma, Japan), Mouse anti-phospho H2AX (yH2AX) antibody, 1:3000 dilution (catalog number: JBW301, manufactured by Millipore, Mass., USA), <Secondary Antibodies>

HRP-labeled anti-rabbit IgG antibody, 1:3000 dilution (catalog number: NA934, manufactured by GE Healthcare, Buckinghamshire, United Kingdom), HRP-labeled anti-mouse IgG antibody, 1:3000 dilution (catalog number: NA931, manufactured by GE Healthcare, Buckinghamshire, United Kingdom).

The primary antibodies and the secondary antibodies together were repeatedly incubated overnight at 4° C. and then incubated for one hour at room temperature. Proteins were detected using a ECL Prime Western blotting detection reagent (catalog number: RPN2232, manufactured by GE Healthcare, Buckinghamshire, United Kingdom) and a lumino-image analyzer (product name: ImageQuant LAS 500, manufactured by GE Healthcare, Buckinghamshire, United Kingdom).

Immunohistochemical Analysis

First, the brains of mice were fixed using 4% paraformaldehyde and were embedded in paraffin. Sagittal or coronal sections (having a thickness of 5 μm) were prepared using a microtome (manufactured by Yamato Kohki Industrial Co., Ltd., Saitama, Japan).

The immunohistochemical analysis was carried out using primary antibodies as follows:

Mouse anti-amyloid β antibody, 1:5000 dilution (clone 82E1, catalog number: 10323, manufactured by IBL, Gunma, Japan), Rabbit anti-HMGB1 antibody, 1:2000 dilution (catalog number: ab18256, manufactured by Abcam, Cambridge, UK), Rabbit anti-Ibal antibody, 1:2000 dilution (catalog number: 019-19741, manufactured by Wako, Osaka, Japan).

The tissue reacted with each antibody was visualized using an Alexa Fluor-488-labeled secondary antibody or an Alexa Fluor-568-labeled secondary antibody (manufactured by Molecular Probes, Mass., USA). Subsequently, amyloid β was visualized using a staining reagent kit for immunohistochemistry (product name: Vectastain Elite ABC kit, catalog number: PK-6100, manufactured by Vector Laboratories, USA) and a peroxidase substrate kit for immunostaining (product name: DAB peroxidase substrate kit, catalog number: SK-4100, manufactured by Vector Laboratories, USA). Nuclei were stained with DAPI (diluted to 0.2 μg/ml with PBS for use, catalog number: D523, manufactured by DOJINDO Laboratories, Kumamoto, Japan).

All images were acquired using a fluorescence microscope (Olympus IX70, Tokyo, Japan), an optical microscope (manufactured by Olympus, Tokyo, Japan), or a confocal microscope (Olympus FV12001X83, Tokyo, Japan).

Fabrication of Hybridoma Clone Producing Anti-HMGB1 Monoclonal Antibody

From mRNA of Wister rats, cDNA encoding the HMGB1 protein (full length) was prepared and subcloned into the pGEX-3X vector (manufactured by GE Healthcare, Buckinghamshire, England). Then, the HMGB1 protein was expressed and purified according to a conventional method. Note that the sequence of the Wister rat-derived HMGB1 protein and the sequence of the mouse-derived one are identical. On the other hand, the sequence of the rat-derived HMGB1 protein and the sequence of the human-derived one are identical except that 2 amino acids are different in the C-terminal positively/negatively charged region.

The HMGB1 protein in an amount of 100 μg was mixed well with an adjuvant, TiterMax (manufactured by CytRx Corporation, L, USA), which was then administered to the footpads of C3H/He and MRL female mice at 6 weeks of age every other day, four times in total for the C3H/He, and five times in total for the MRL, for the immunization. Two days after the last administration, lymphocytes were prepared from immune mice and were fused to mouse myeloma cells by the PEG method. The fused cells were cultured on 96-well microplates with a selective medium containing FCS, aminopterin, streptomycin, and penicillin for about 2 weeks under the conditions of 37° C. and 5% $CO_2$.

Then, to select anti-HMGB1 monoclonal antibodies, the ELISA method was carried out as described below. First, part of the culture solution after 2 weeks was sampled and added in 500 µL/well to a microplate in which 250 ng/well of the HMGB1 protein or the negative control protein (GST) was immobilized. Subsequently, reaction was carried out at room temperature for 1 hour, followed by washing with PBS three times. A secondary antibody (HRP-labeled anti-mouse IgG, manufactured by MEDICAL & BIOLOGICAL LABORATORIES CO., LTD., code number 330) was diluted in accordance with the package insert and added in 50 µL/well, which was reacted for one hour at room temperature, followed by washing with PBS three times after the reaction. Thereafter, a TMB reagent (MOSS, Inc., Chicago, Ill., USA) was added in 50 µL/well, followed by enzyme chromogenic reaction for 15 minutes. Subsequently, after the enzyme reaction was stopped with 1.5 N phosphoric acid, the absorbance was measured with a plate reader with 450 nm (reference 630 nm) to select clones that reacts specifically with the HMGB1 solid-phase plate, establishing anti-HMGB1 monoclonal antibodies.

Note that from about 1000 clones of the hybridoma prepared as described above, 10 clones were selected as shown in Table 1 through three times of screening by the ELISA method.

Pathological Analysis on Spines Using Two-photon Microscope

An adeno-associated virus 1 (AAV1)-EGFP (titer: $1 \times 10^{10}$ vector genome/mL, 1 µL) having a synapsin 1 promoter was injected to the retrosplenial cortices of mice (at 22 weeks of age) (at a position anteroposteriorly −2.0 mm and mediolaterally 0.6 mm away from the bregma to a depth of 1 mm) which were anesthetized with 2.5% isoflurane.

After two weeks, a thinly ground circular portion was prepared in the skull bone at a mouse retrosplenial cortex using a high-speed micro drill. Then, the head of the mouse was fixed by attaching a head plate to the stage of a custom machine mounted on the microscope table.

The two-photon imaging was carried out using a scanning laser microscope system FV1000MPE 2 (manufactured by Olympus) equipped with an upright microscope (BX61WI, manufactured by Olympus, Japan), a water immersion objective (XLPlanN25xW; numerical aperture, 1.05), and a pulse laser (MaiTai HP DeepSee, manufactured by Spectra Physics, USA).

The EGFP was excited by light having a wavelength of 890 nm and scanned in a range of 500 to 550 nm. The region scanned for the three-dimensional imaging was of 100×100 µm (1 µm Z-axis step, 1024×1024 pixels).

The high magnification imaging (101.28 µm×101.28 µm; 1024×1024 pixels; 1 µm Zstep) of the first layer (layer 1) of the cerebral cortex was observed through the observation

TABLE 1

|  | Total Number of Selected Clones | MRL-derived | | C3H/He-derived | |
| --- | --- | --- | --- | --- | --- |
|  |  | Number of Selected Clones | Selection Criteria (O.D.) | Number of Selected Clones | Selection Criteria (O.D.) |
| ELISA 1st | 67 | 31 | 0.03 or more | 36 | 0.09 or more |
| ELISA 2nd | 20 | 8 | 0.04 or more | 12 | 0.2 or more |
| ELISA 3rd | 10 | 1 | Posi: 0.2 or more, Nega: 0.1 or less | 9 | Posi: 0.2 or more, Nega: 0.1 or less |

Purification of Antibodies

The selected hybridoma clones were cultured in a serum-free medium (product name: Hybridoma-SFM, manufactured by ThermoFisher Scientific, Mass., USA). From the medium after the expansion culturing of the selected clones, cell debris was removed by a centrifugal treatment.

The monoclonal antibodies in the semi-purified growth medium were bound to an antibody purifying affinity support (product name: rProtein A Sepharose Fast Flow resin, manufactured by GE Healthcare, Buckinghamshire, England) overnight using a circulation pump.

Then, after the column was washed with a 10× volume PBS, the monoclonal antibody bound to the support was eluted with 0.1 M sodium citrate (pH 4.0). The obtained product was then neutralized with 1.0 M Tris-HCl (pH 9.0) and subjected to a dialysis with PBS in accordance with the recommended protocol.

Subcutaneous Injection of Anti-HMGB1 Monoclonal Antibody

The anti-HMGB1 monoclonal antibody was injected in a concentration of 1 mg/kg to 5×FAD mice or B6/SJL mice at the dorsal neck regions, during 1 to 6 months of age or during 3 to 6 months of age, once a week. In the same way, mice to which control IgG (a mouse IgG2a antibody purified from a hybridoma cell line with a protein A, manufactured by MBL) was injected were prepared as a control group.

window in the thinly ground skull bone at the retrosplenial cortex with 5× digital zooming.

Transition of Biotin-labeled Antibody to Plasmas and Brains

Biotin-labeled mouse IgG (Product number; SAB3700901, manufactured by Sigma-Aldrich, Mo., USA) was subcutaneously injected in the same manner as the above-described anti-HMGB1 monoclonal antibody was. The sampling of the plasmas and the brain tissues was conducted on day 1 and day 3. A sandwich ELISA system was built up in order to detect the transition to the plasmas and the brain tissues.

Y-maze Test

In this test, the mice were caused to take an exploratory behavior on a Y-shaped maze having three identical arms arranged at an identical angle between each two arms (manufactured by O'HARA & Co., Ltd., Tokyo, Japan). Specifically, mice at 6 months of age were placed at the end of one arm and allowed to move freely through the maze during an active phase of 8 minutes. The percentage of spontaneous alternations (indicated as alternation rate) was calculated by dividing the number of times when the mouse entered a new arm different from an arm where the mouse entered previously by the total number of times when the mouse moved from one arm to another arm.

Preparation of Different Species

Aβ oligomers, protofibrils/ADDLs, and aggregates/fibrils were prepared in accordance with the method described in Klein, W. L., Neurochem. Int. 41, 345-352 (2002).

To explain it briefly, a lyophilized amyloid $\beta_{1-42}$ ($A\beta_{1-42}$) protein (manufactured by Peptide Institute, Osaka, Japan) was dissolved in DMSO (manufactured by Sigma, Mo., USA) and prepared as a 1 mM stock solution. The $A\beta_{31-42}$ stock solution was diluted to 100 μM for cell culture and was also diluted to 30 μM for in vitro analysis using PBS. The solution was further incubated at 5° C. for 24 hours to form oligomers and ADDLs, and was further incubated at 37° C. for 24 hours to form aggregates/fibrils.

Tris-Tricine SDS-PAGE

Aβ formation was tested by Tris-Tricine SDS-PAGE in accordance with the method described in Schagger, H. Tricine-SDS-PAGE. Nat. Protoc. 1, 16-22 (2006).

To explain it briefly, a electrophoresis gel containing 0.1% SDS, 0.1 g/ml of glycerol, and 1M Tris was adjusted to a pH of 8.45 with HCl. In addition, 16%, 10%, and 4% gels were used in a layered manner in this order from bottom. Then, AR samples were fractionated with the Tris-Tricine SDS-PAGE using an anode buffer of 1M Tris-Cl (pH 8.9) and a cathode buffer of 1M Tris and 1M Tricine.

Transmission Electron Microscope

Each sample in the in vitro aggregation assay was fixed with 2% glutaraldehyde and placed on a 300-mesh copper grid coated with formvar for 1 minute. Subsequently, the sample was washed with water and subjected to negative staining with 1% uranyl acetate for 1 minute. Then, the sample was observed using a transmission electron microscope (manufactured by HITACHI, H-7100, Tokyo, Japan) operated at 80 kV.

Immunoelectron Microscopy

Each sample in the in vitro aggregation assay was placed on a nickel grid and fixed with 1% PFA in 0.1 M phosphoric acid buffer at room temperature. After washing with 0.1 M Tris-Hcl (pH 7.5), the sample was incubated in 5% goat serum in 0.1 M Tris-HCl for 10 minutes to exclude non-specific binding of the antibody.

The sample was incubated together with the primary antibody in 5% goat serum in 0.1 M Tris-Hcl (pH 7.5) at room temperature for 2 hours. After washed with 0.1 M Tris-Hcl (pH 7.5), the sample was incubated together with the secondary antibody in 0.1 M Tris-Hcl (pH 7.5) at room temperature for one hour.

Note that as the primary antibody, a mouse anti-Aβ antibody (1:50 dilution, clone 6E10, Product Code: SIG-39300, manufactured by Covance, N.J., USA) or a rabbit anti-HMGB1 antibody (1:50 dilution, ab18256, manufactured by Abcam, Cambridge, UK)] was used.

In addition, as the secondary antibody, a 10 nm gold-labeled anti-mouse (1:100 dilution, EM GAF 10, manufactured by BB International, Cardiff, UK) or a 5 nm gold-labeled anti-rabbit (1:100 dilution, EM GAR 5, manufactured by BB International, Cardiff, UK) was used.

Each sample was subjected to negative staining with 1% uranyl acetate for 1 minute to be observed with the transmission electron microscope.

Phagocytosis of Aβ by Microglia

The primary cultured cortical neuron was prepared from Wister rats in accordance with the method described in Nakajima, K. et al., Glia 24, 272-289 (1998), followed by inoculation into a 8-well chamber glass slide (product name: Lab-Tek II, manufactured by Nalgene, Ill., USA) without coating to obtain $2\times10^4$ cell/well.

A pre-incubated TAMRA-Aβ (10 nM, product number: AK13A, manufactured by Cosmo Bio Co. Ltd., Tokyo, Japan), a TAMRA-Aβ/HMGB1 (10 nM each), or a TAMRA-Aβ/HMGB1/anti-HMGB1 monoclonal antibody (10 nM each) was added to the primary culture cell. After 45 minutes, the cells were fixed with 1% PFA for 20 minutes.

Images were obtained using Olympus FV1200-IX83 (manufactured by Olympus, Tokyo, Japan). The percentage of TAMRA-Aβ-incorporated microglia was calculated in a field number of 10 of a 20× objective image and the number of TAMRA-Aβ-incorporated microglia in each group was counted.

Statistical Analysis

In the biological analysis, data was represented as the mean value+/− standard error in consideration of whether the data conformed to a normal distribution. The Student's t-test was applied for 2 groups comparisons. For multiple group comparisons, the Tukey's HSD test or the Dunnette's test was used. The significance level was set to 1% or 5%.

Ethics

This study was performed in strict accordance with the recommendations in the Guide for the Care and Use of Laboratory Animals of the National Institutes of Health. It was approved by the Committees on Gene Recombination Experiments, Human Ethics, and Animal Experiments of the Tokyo Medical and Dental University (Numbers: 2010-215C14, 2014-5-4 and 0160328C, respectively).

(Preparation of Anti-HMGB1 Antibodies and Determination of Sequences of Anti-HMGB1 Antibodies)

Figure 1B:
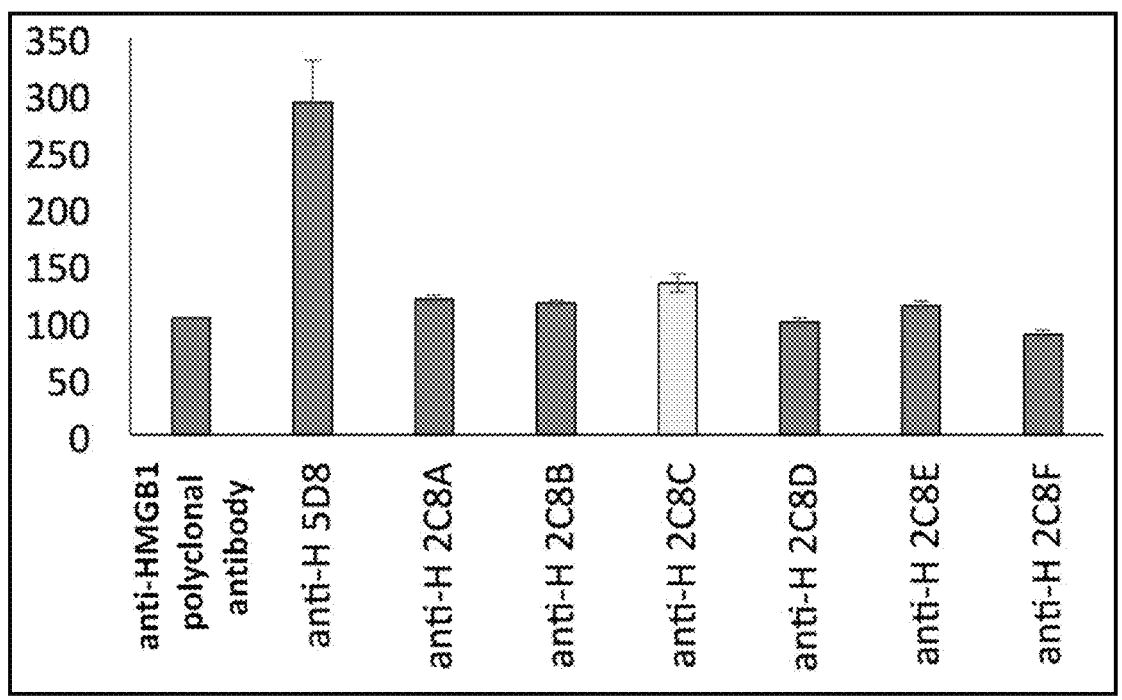
FIG. 1B is a graph showing the result of comparing 7 clones of the anti-HMGB1 antibody in terms of affinity for HMGB1 by a surface plasmon resonance (SER) analysis. In the figure, the vertical axis shows the binding response (resonance unit, RU).

To evaluate the effectiveness of antibody therapy targeting HMGB1 in Alzheimer's disease (AD), the clone 2C8C was selected based on the result of binding assay for 10 clones selected from multiple HMGB1 antibodies prepared as described above (see FIGS. 1A and 1B. The results of 7 clones among 10 clones are disclosed in FIGS. 1A and 1B). Note that clone 2C8C was derived from C3H/He mice.

Figure 2:
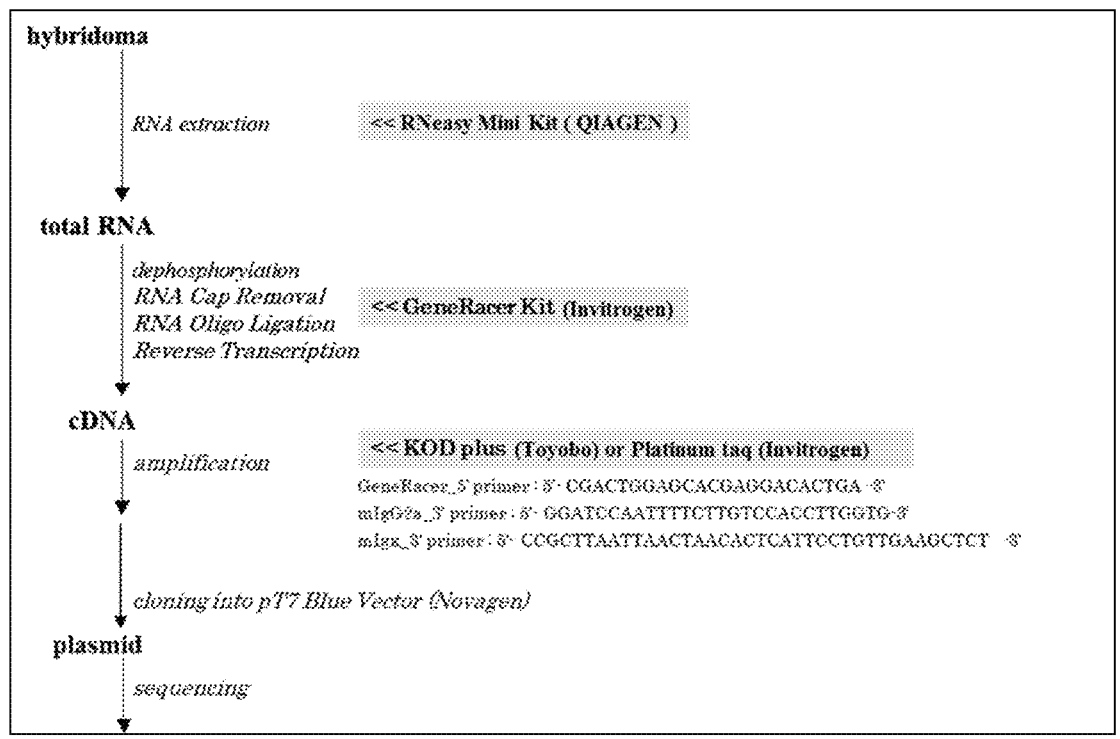
FIG. 2 is a schematic diagram showing steps of isolating an antibody gene from a hybridoma producing an anti-HMGB1 monoclonal antibody (2C8C) and identifying the sequence of the gene. Note that the DNA sequences of the primers in the diagram are shown in SEQ ID NOs: 13 to 15, respectively.

Then, in accordance with the method shown in FIG. 2, DNA encoding the variable region and the constant region was amplified with PCR and acquired from hybridoma (2C8C) for the heavy chain and the light chain, and was subjected to the sequencing analysis. As a result, as shown in FIGS. 3 and 4, the amino acid sequences of the variable regions of the heavy chain and the light chain as well as CDR of the anti-HMGB1 monoclonal antibody (2C8C antibody) were successfully identified. Note that CDR was predicted based on the kabat rule. In addition, each sequence identified was specified by the following SEQ ID NOs.

The nucleotide sequence encoding the light chain (signal peptide, variable region and constant region) of the 2C8C antibody . . . SEQ ID NO: 1, The amino acid sequence of the light chain (signal peptide, variable region and constant region) of the 2C8C antibody . . . SEQ ID NO: 2, The amino acid sequence of the light chain (variable region) of the 2C8C antibody . . . SEQ ID NO: 3, The amino acid sequences of the light chain (CDR1 to CDR3 of variable region) of the 2C8C antibody . . . SEQ ID NOs: 4 to 6, The nucleotide sequence encoding the heavy chain (signal peptide, variable region and constant region) of the 2C8C antibody . . . SEQ ID NO: 7, The amino acid sequence of the heavy chain (signal peptide, variable region and constant region) of the 2C8C antibody . . . SEQ ID NO: 8, The amino acid sequence of the heavy chain (variable region) of the 2C8C antibody . . . SEQ ID NO: 9, The amino acid sequences of the heavy chain (CDR1 to CDR3 of variable region) of the 2C8C antibody . . . SEQ ID NOs: 10 to 12.

(Effectiveness of Antibody Therapy Targeting HMGB1 in Alzheimer's Disease)

Figure 5A:
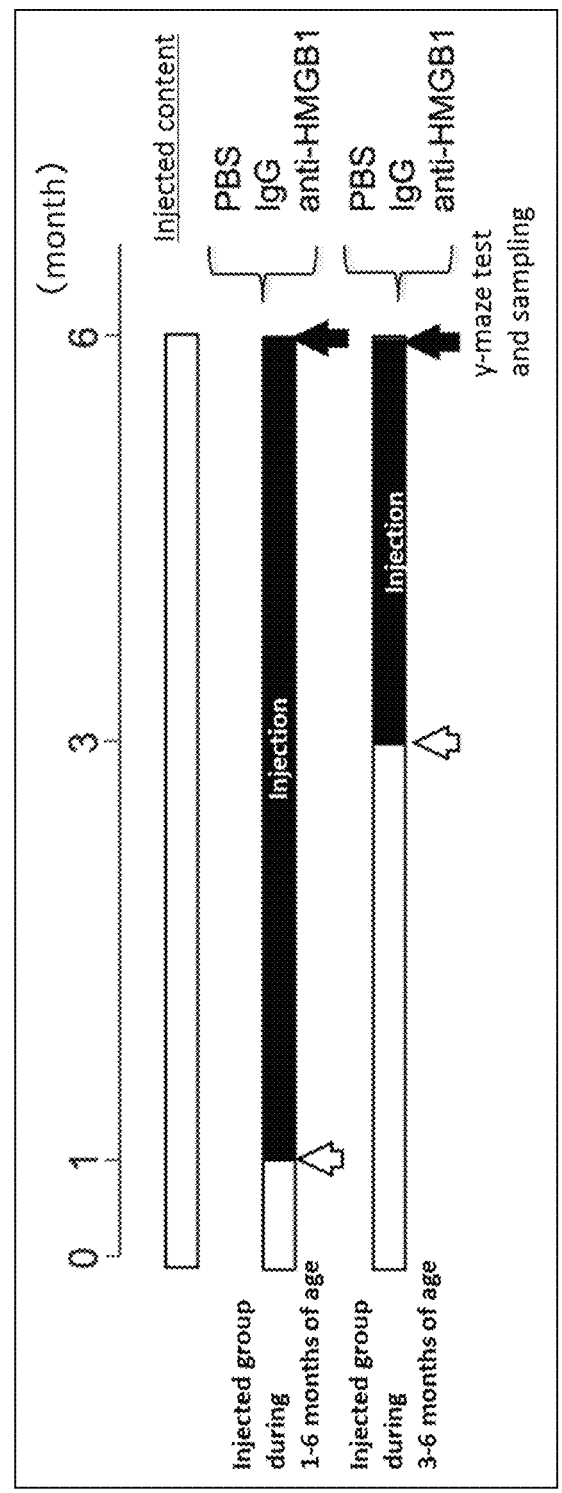
FIG. 5A is a schematic diagram showing a treatment protocol for AD model mice by subcutaneous injection of the anti-HMGB1 antibody. The mice subjected to this protocol were grouped into a non-injected group and injected groups (a PBS injected group, a control IgG injected group, and an anti-HMGB1 antibody injected group). The injected groups were further grouped into a group in which injection was conducted during 1 to 6-months of age and a group in which injection was conducted during 3 to 6-months of age. The injection was conducted once a week and the dose of one injection was 1 mg/kg. The Y-maze test is an only method for detecting memory disturbance at the early stage. This test was conducted based on the previous report (Oakley, H. et al., J Neurosci 26, 10129-10140 (2006)) and the alternation rates of mice at 6 months of age in the Y-maze were determined.

Next, by subcutaneously injecting the anti-HMGB1 antibody thus obtained to AD mouse model (5×FAD mice) through 2 types of protocols shown in FIG. 5A, it was evaluated whether the symptoms and phenotype of Alzheimer's disease (AD) in the mouse model were ameliorated.

Figure 6A:
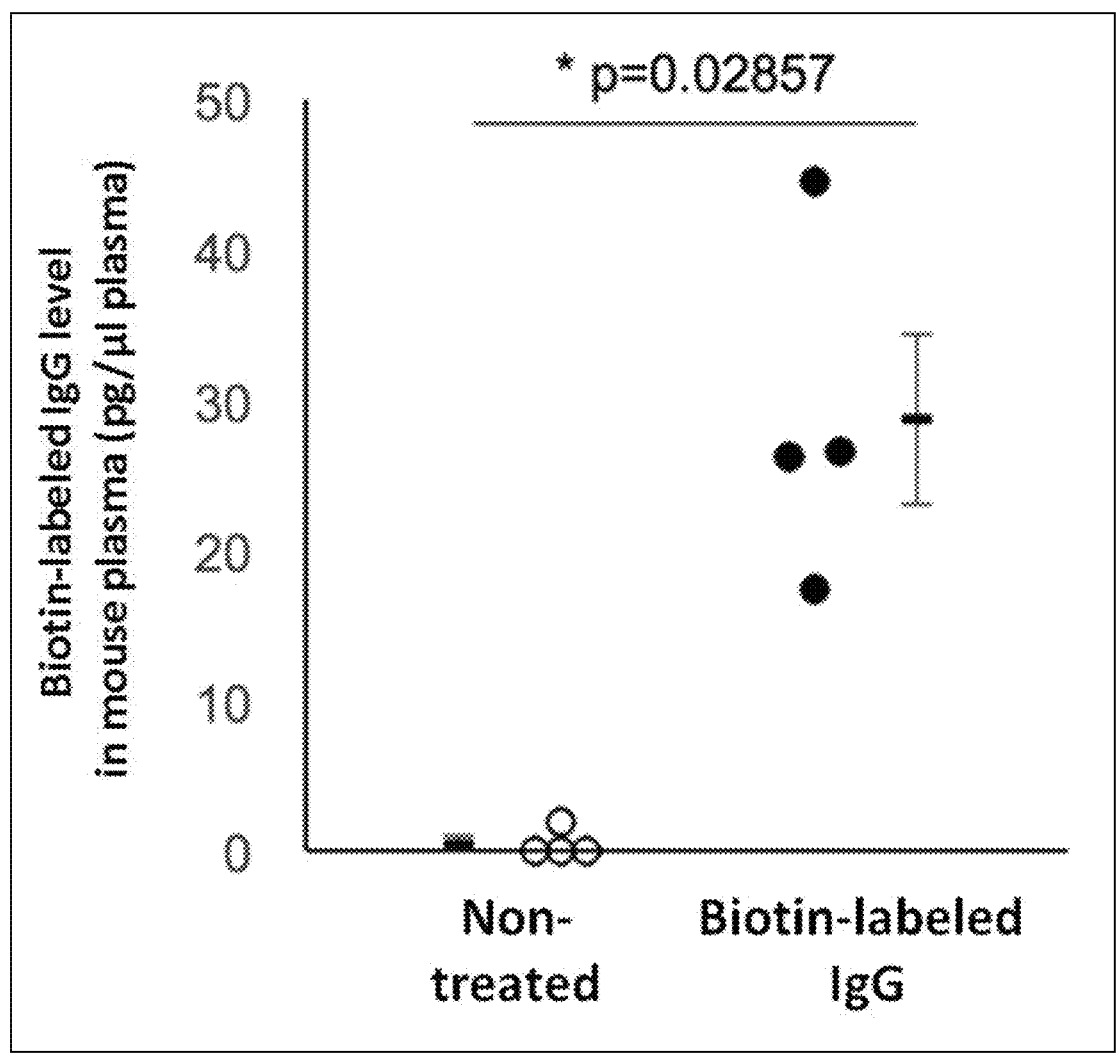
FIG. 6A is a graph showing the concentrations of the biotin-labeled IgG in the plasmas of mice and the like on day 3 after the IgG was subcutaneously injected to the mice. In the figure, "non-treated" shows the result of a mouse to which the IgG was not injected (negative control). The white circles indicate the detectable minimal value. In addition, the P values were calculated by the Wilcoxon rank sum test and the Fisher's exact test (regarding the captions in the figures, the same applies to FIG. 6B as well).
Figure 6B:
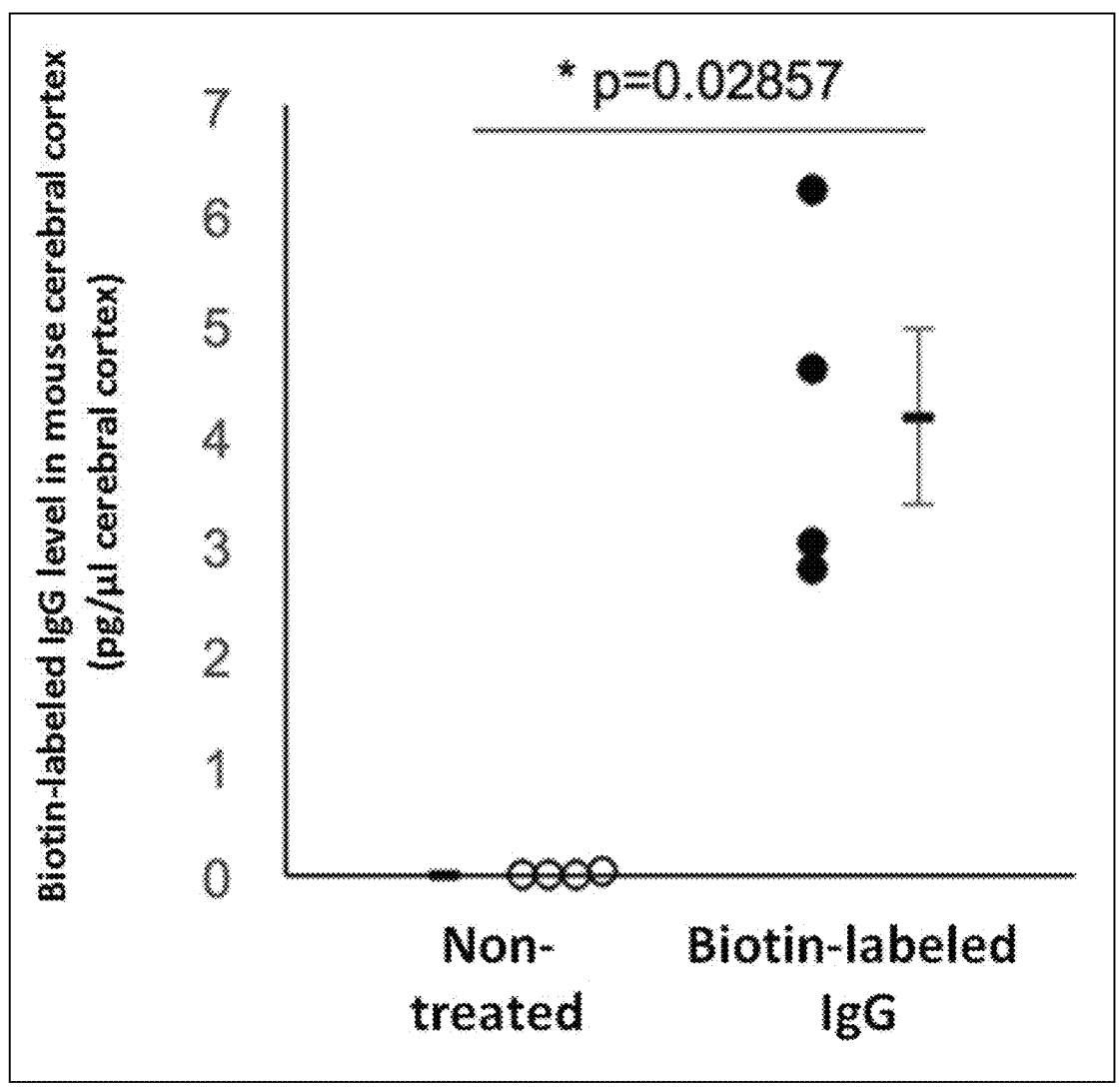
FIG. 6B is a graph showing the concentrations of the biotin-labeled IgG in the cerebral cortices of mice and the like on day 3 after the IgG was subcutaneously injected to the mice. Some of the injected IgG was detected (0.008%) in the brain tissue prepared after systemic perfusion with the PBS.
Figure 6C:
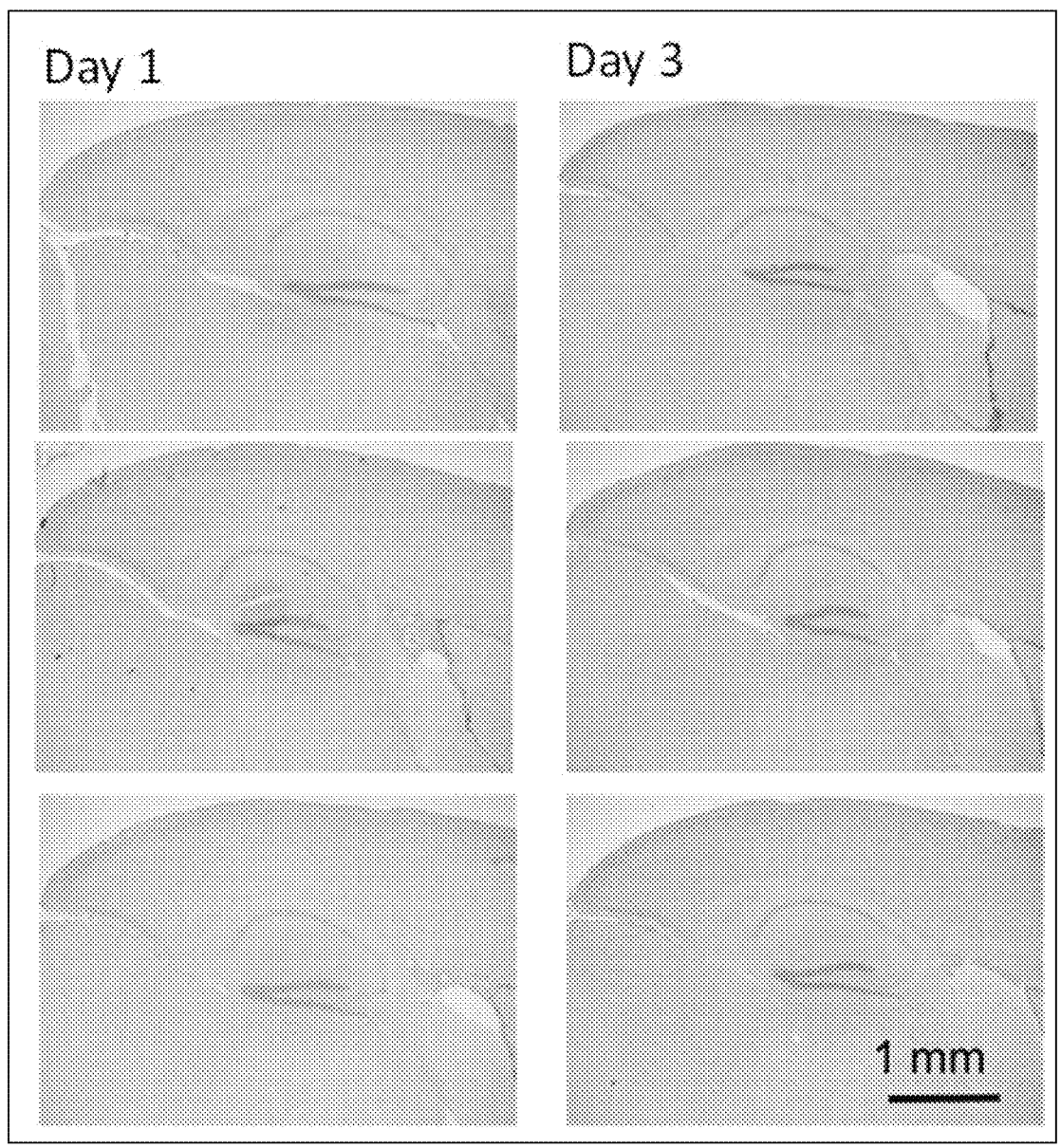
FIG. 6C is photographs showing the result of conducting the immunohistochemical analysis with the avidin-HRP and DAB color development in the brain tissue to detect the biotin-labeled IgG in mice to which the IgG was subcutaneously injected. The mice used were C57BL/6j male (at 2 months of age) and the biotin-labeled mouse IgG (1 mg/kg) was subcutaneously injected to the mice. The brain tissue on day 1 or day 3 (n=3) after the injection was fixed with paraformaldehyde (PFA) and embedded in paraffin. Then, 5 µm sections were prepared and immunohistochemical analysis with avidin-HRP and DAB color development was performed to detect the IgG. As a result, as shown in FIG. 6C, no definite signal was detected.

Note that as a result of analyzing whether the biotin-labeled IgG is delivered with ELISA in a similar method, it was confirmed that the concentration of IgG was improved in the plasmas and brain tissues by subcutaneous injection (see FIGS. 6A and 6B); however, no confirmation was made in the immunohistochemical analysis (see FIG. 6C).

Figure 5B:
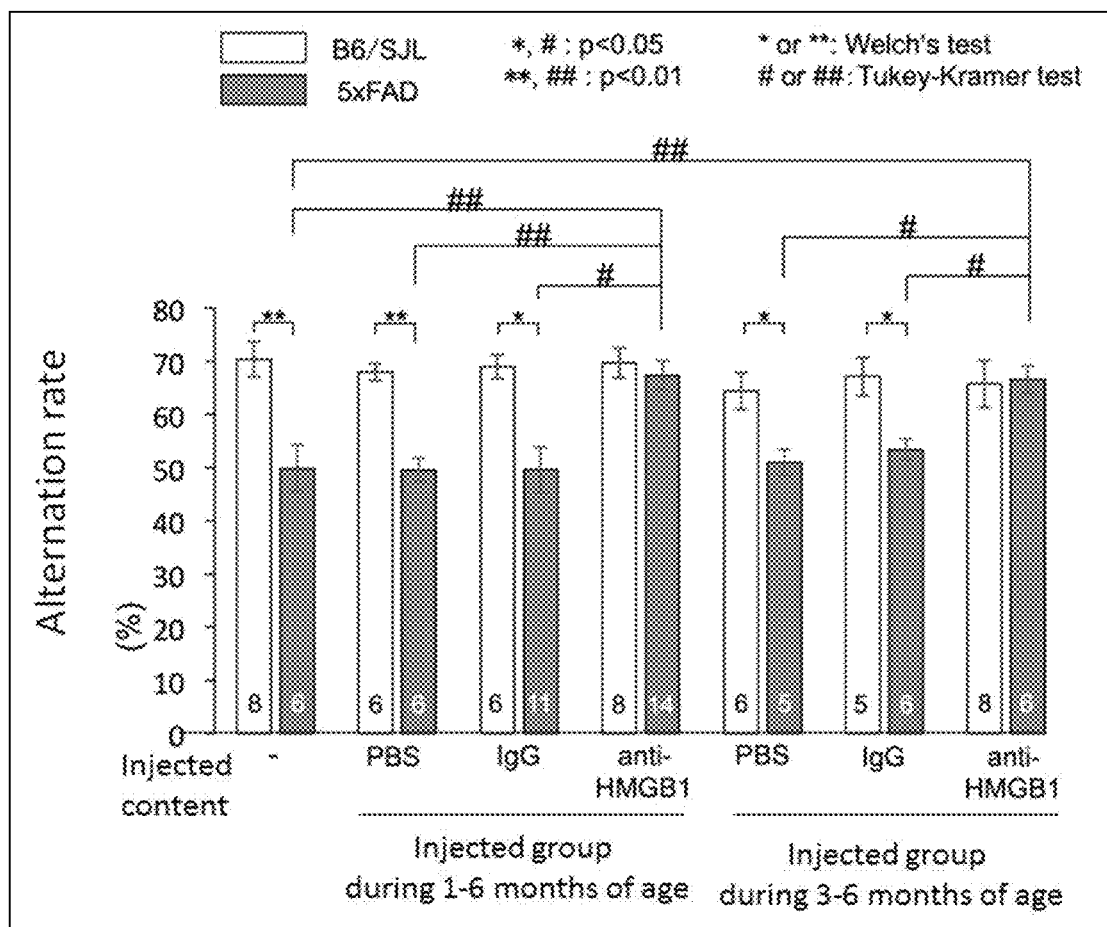
FIG. 5B is a graph showing alternation rates of the group of mice to which the anti-HMGB1 antibody and the like were injected (injection periods: 1 to 6-months of age and 3 to 6-months of age) in the Y-maze test. As shown in this figure, the alternation rates were reduced to the normal level (B6/SJL) in AD model mice (5×FAD mice) to which the anti-HMGB1 antibody and the like were injected. On the other hand, in the AD model mice, no effects of injection of PBS or IgG were observed.

As reported in Oakley, H. et al., J Neurosci 26, 10129-10140 (2006), the Y-maze test sensitively detected the onset in 5×FAD at 6 months of age. As shown in FIG. 5B, subcutaneous injection of the anti-HMGB1 antibody improved the cognitive impairments of 5×FAD mice to the level of wild-type mice in both two protocols.

Figure 5C:
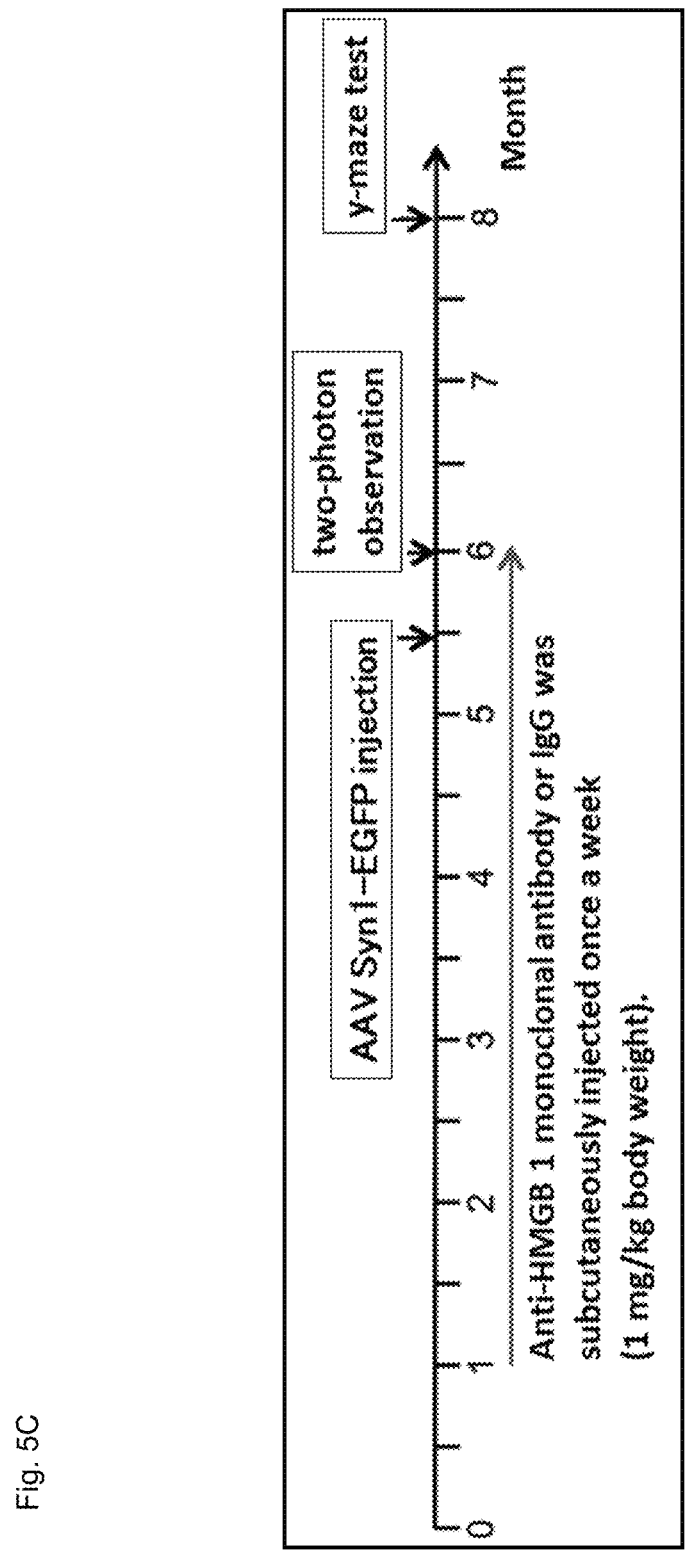
FIG. 5C is a schematic diagram showing the protocol for analyzing dendritic spines in the AD model mice and the like using a two-photon microscope.
Figure 5D:
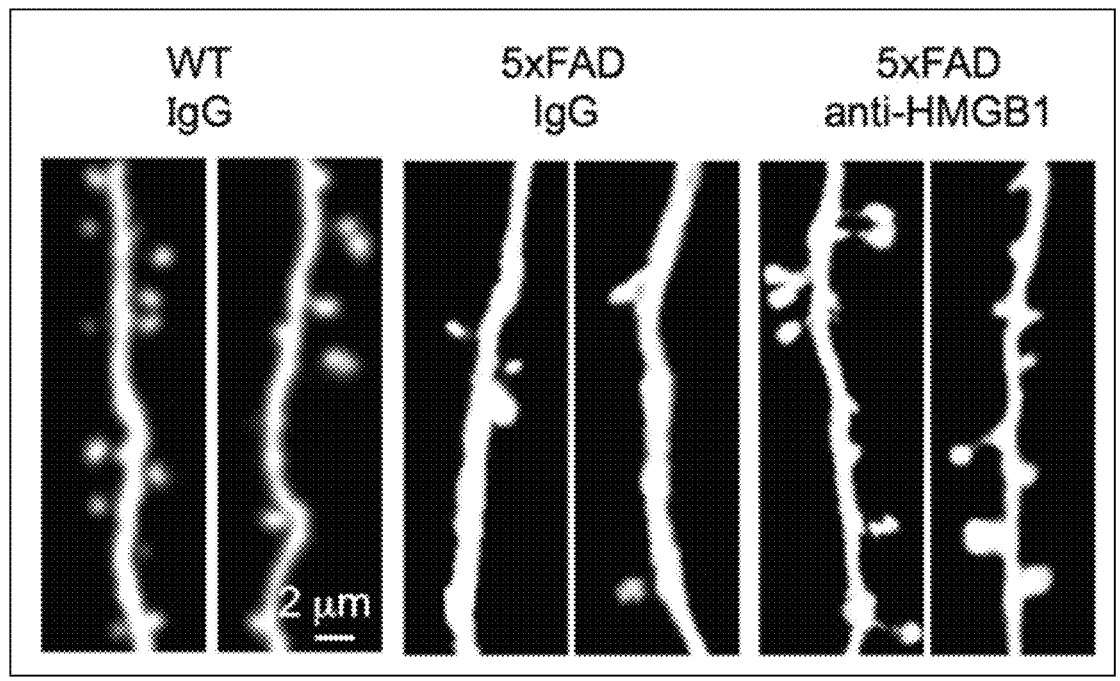
FIG. 5D is photographs showing the result of analyzing the dendritic spines in the independent 5×FAD mouse group and the like using the two-photon microscope. In the figure, "WT IgG" shows the result of injecting IgG to wild-type mouse (B6/SJL), "5×FAD IgG" shows the result of injecting IgG to the AD model mouse, and "5×FAD anti-HMGB1" shows the result of injecting the anti-HMGB1 antibody to the AD model mouse (regarding the captions in the figures, the same applies to FIG. 5E and FIG. 5F as well).
Figure 5E:
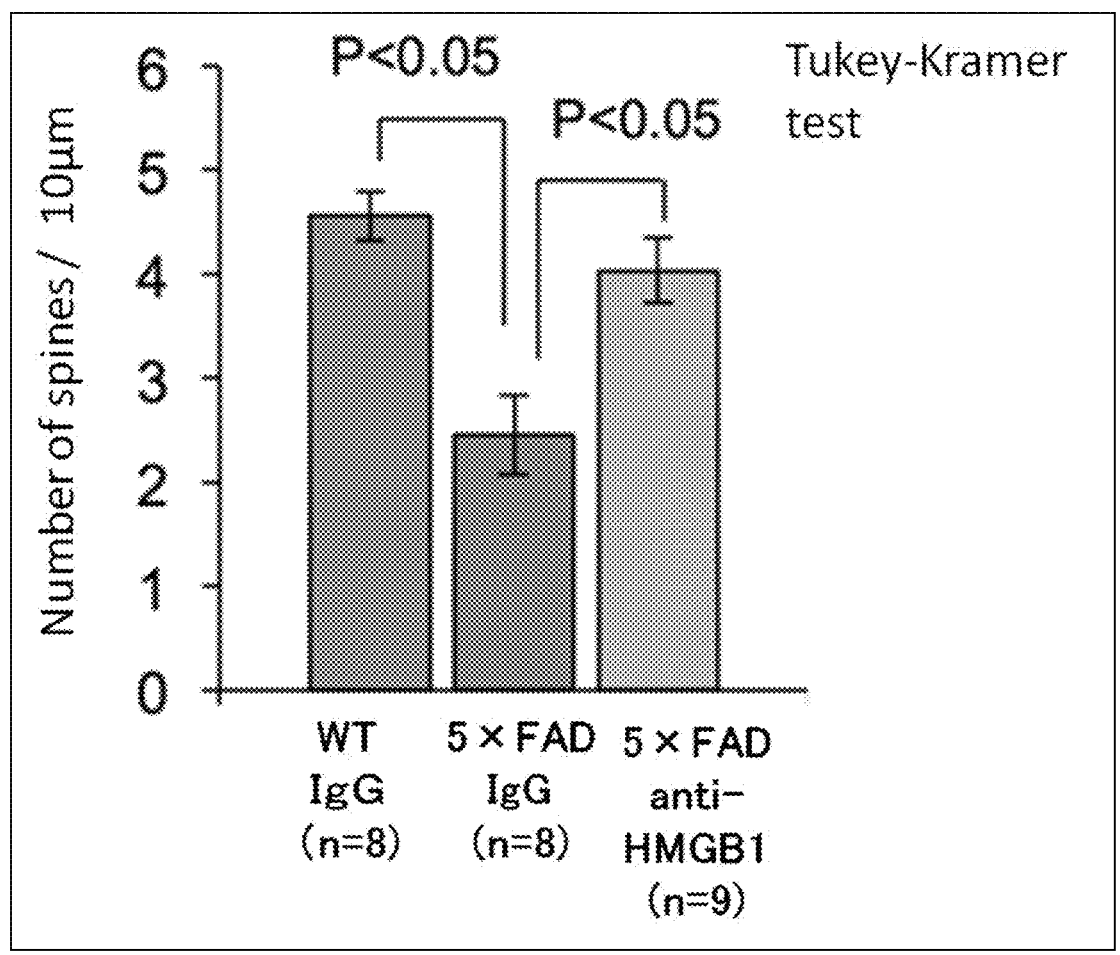
FIG. 5E is a graph showing the result of analyzing the dendritic spines of the independent AD model mouse group and the like using the two-photon microscope. Injecting the anti-HMGB1 antibody during 1 to 6 months of age based on the protocol shown in FIG. 5C recovered the spine density in the 5×FAD mice at 6 months of age as shown in FIGS. 5D and E.
Figure 5F:
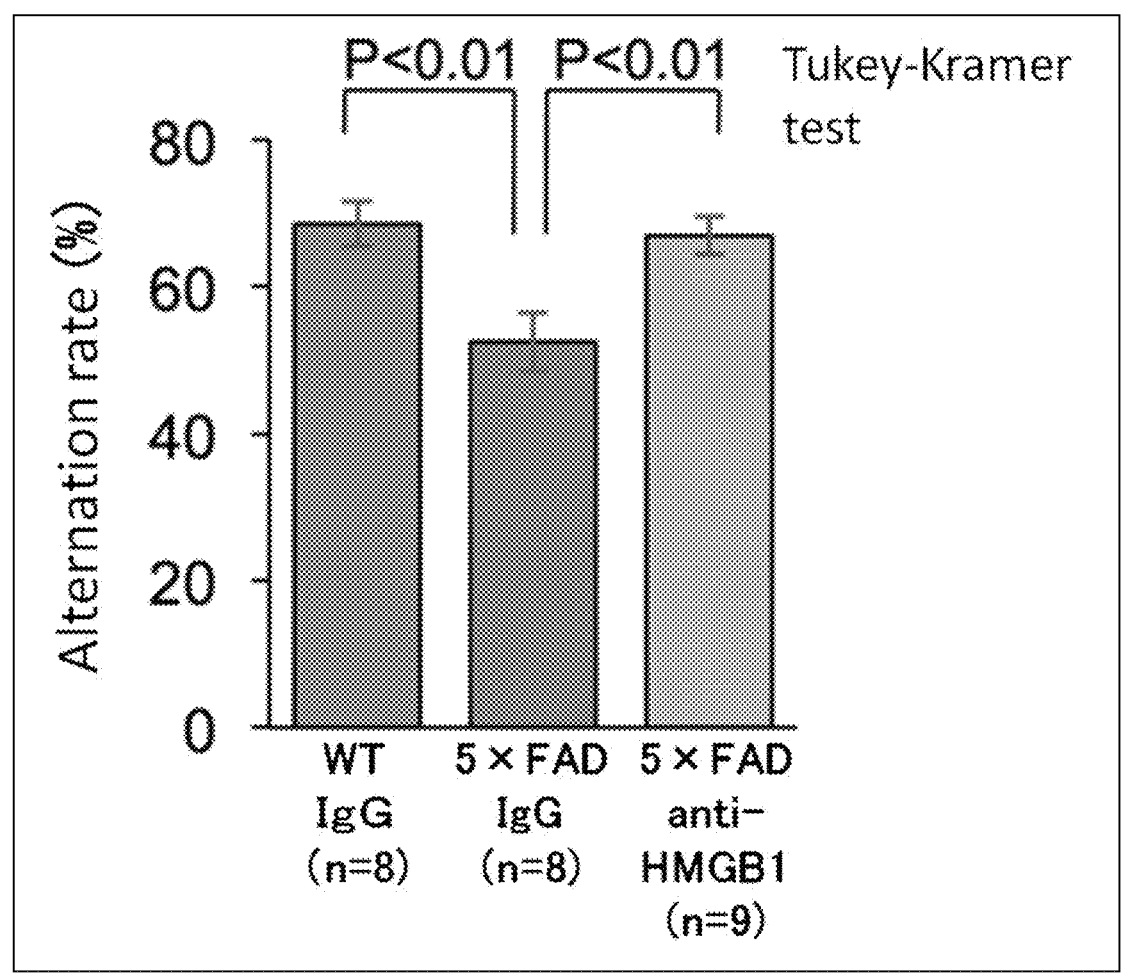
FIG. 5F is a graph showing the results of testing the mice used in the above two-photon microscope analysis with the Y-maze at 8 months (32 weeks) after the mice were further bred for another 8 weeks. As shown in this figure, the memory disturbances of the 5×FAD mice were still ameliorated.

Moreover, consistent with the results of the Y-maze test, the effect of the antibody in the spine morphology was also revealed in a different subcutaneously injected groups of the same antibody by two-photon excitation microscopy (see FIGS. 5C to 5E). Furthermore, the recovery of cognitive impairment in the Y-maze test was confirmed in other series of experiments (see FIG. 5F).

Figure 5G:
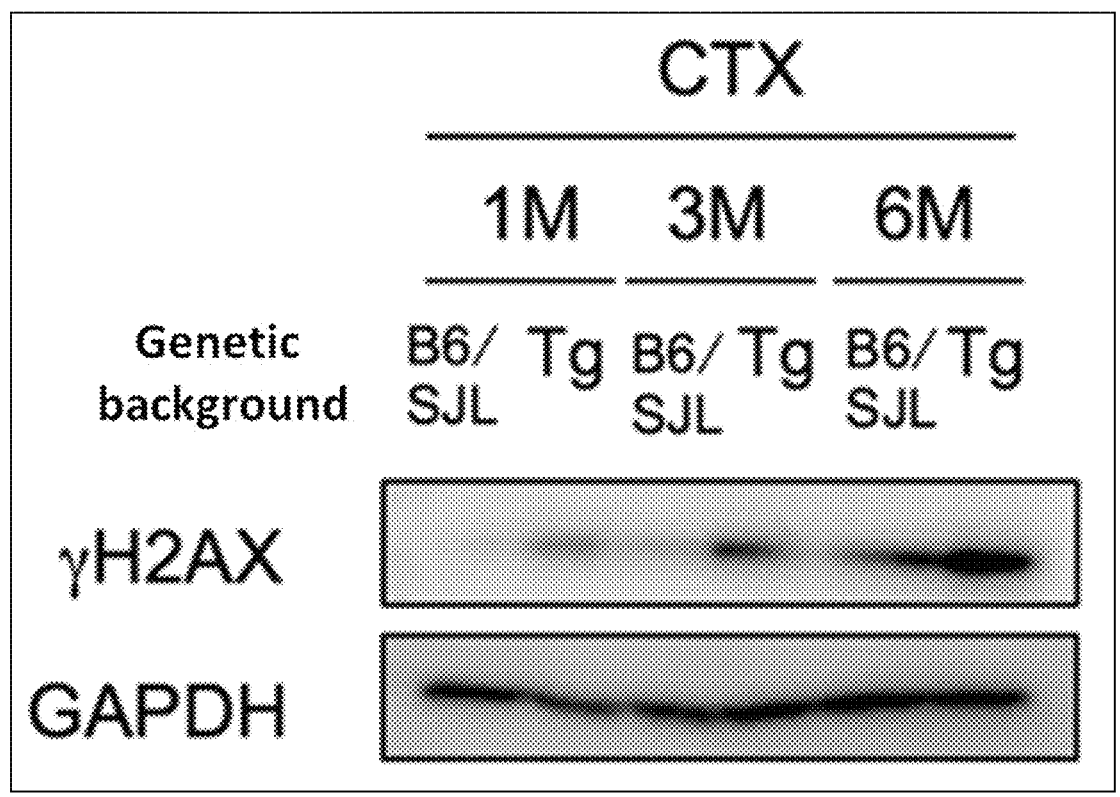
FIG. 5G is photographs showing the results of detecting the DNA damage marker γH2AX in the cerebral cortices (CTXs) of mice (at 1 month of age (1M), 3 month of age (3M), and 6 month of age (6M)) with the Western blot. In the figure, "Tg" shows the result of analyzing the 5×FAD mouse, and "B6/SJL" shows the result of analyzing the wild-type mouse.
Figure 5H:
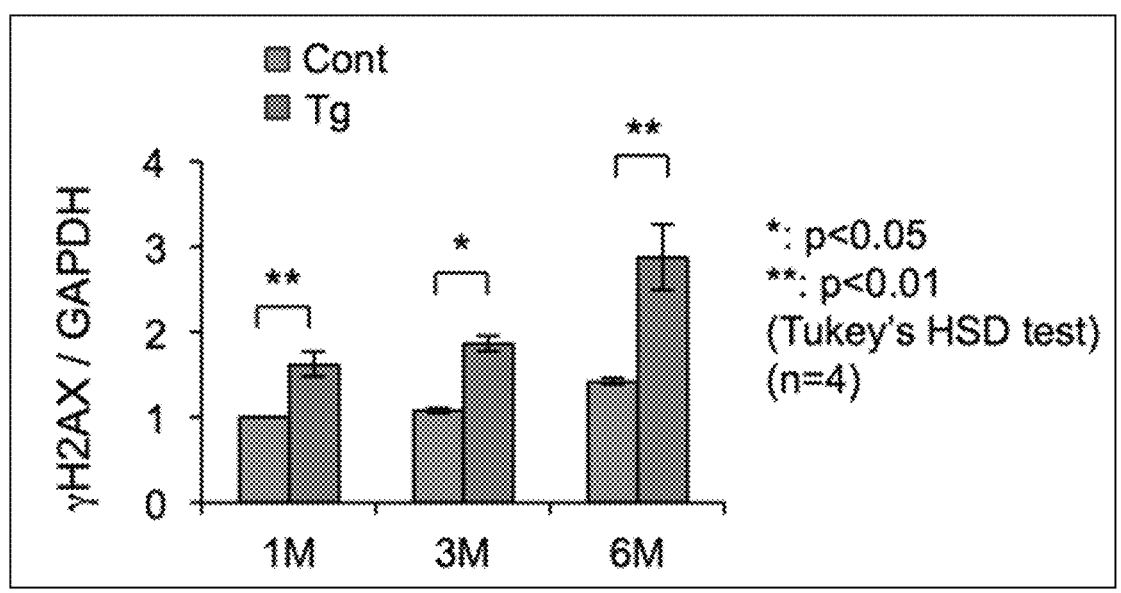
FIG. 5H is a graph showing the results of detecting the DNA damage marker γH2AX in the cerebral cortices (CTX) of mice (at 1 month of age (1M), 3 month of age (3M), and 6 month of age (6M)) with the Western blot. In the figure, the right bar "Tg" in each group (1M, 3M, 6M) shows the result of analyzing the 5×FAD mice and the left bar "Cont" shows the result of analyzing the wild-type mice. The vertical axis shows the relative value representing the amount of γH2AX detected with the Western blot to the amount of GAPDH as a reference.
Figure 5I:
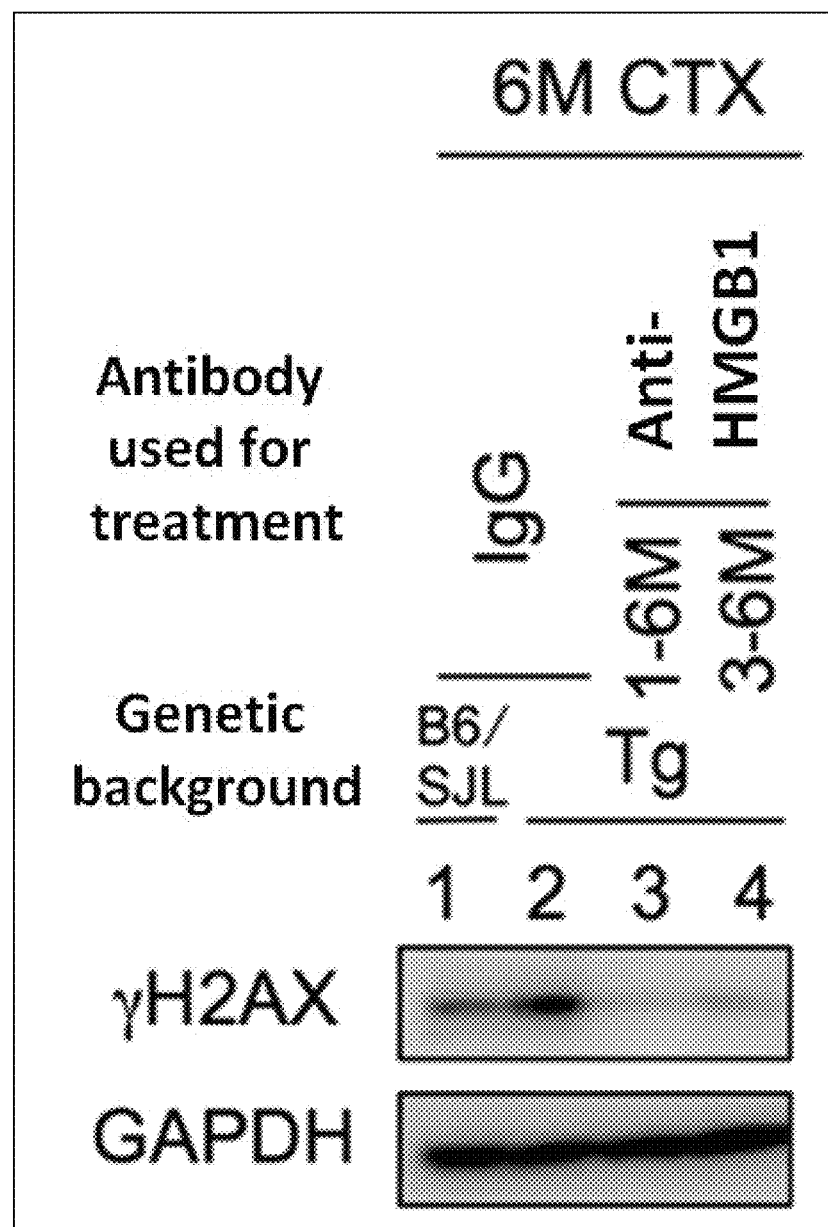
FIG. 5I is photographs showing the results of detecting the DNA damage (γH2AX) in the cerebral cortices of 5×FAD mice at 6 months of age and the like to which the anti-HMGB1 antibody was subcutaneously injected during 1 to 6 months of age or during 3 to 6 months of age with the Western blot. In the figure, "1" shows the result of injecting control IgG to the wild-type mouse (B6/SJL), "2" shows the result of injecting control IgG to the 5×FAD mouse (Tg), "3" shows the result of injecting the anti-HMGB1 antibody to 5×FAD mouse during 1 to 6 months of age, and "4" shows the result of injecting the anti-HMGB1 antibody to 5×FAD mouse during 3 to 6 months of age (regarding the captions in the figures, the same applies to FIG. 5J as well).
Figure 5J:
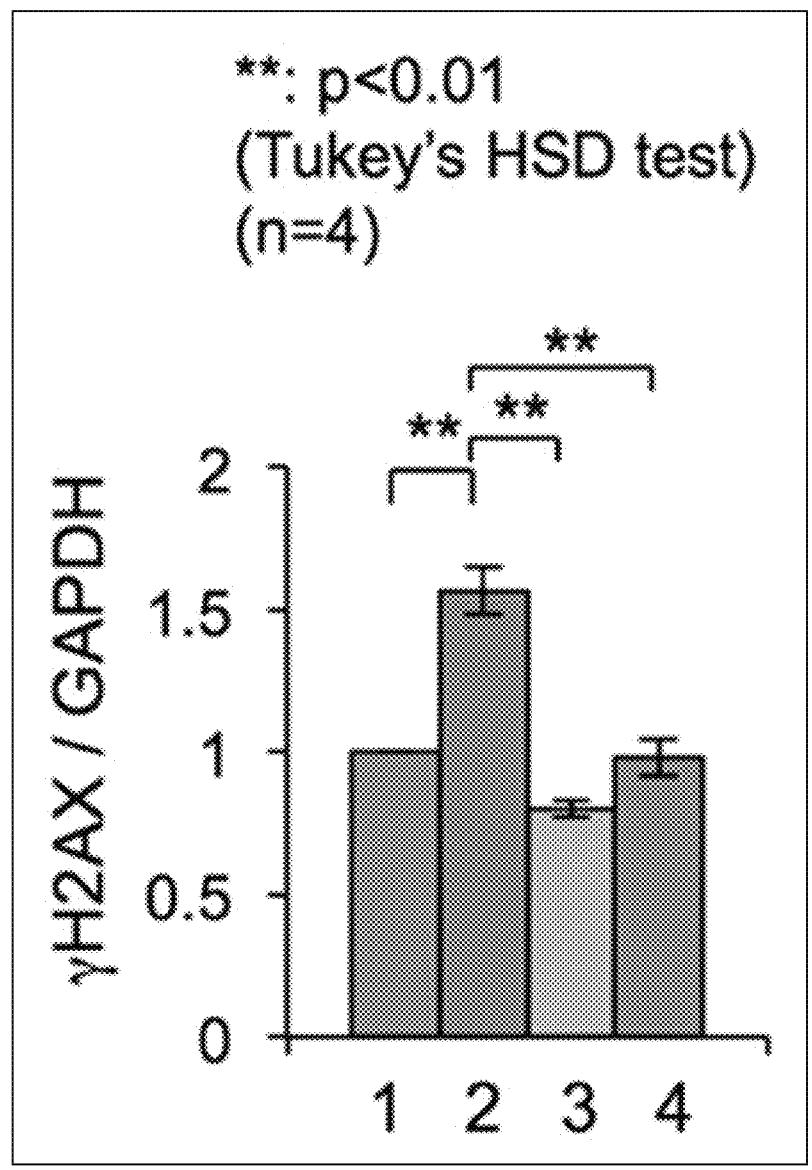
FIG. 5J is a graph showing the result of detecting the DNA damage (γH2AX) in the cerebral cortices of the 5×FAD mice at 6 months of age and the like to which the anti-HMGB1 antibody was subcutaneously injected during 1 to 6 months of age or during 3 to 6 months of age with the Western blot. Note that the vertical axis in the figure shows the relative value representing the amount of γH2AX detected with the Western blot to the amount of GAPDH as a reference.

In addition, it was also revealed that the anti-HMGB1 antibody reduced DNA damage in the cerebral cortex as shown in FIGS. 5I and 5J. Note that DNA damage increases with time in normal mice, and the extent of the increase is higher in AD mice at all ages (see FIGS. 5G and H). However, injection of the anti-HMGB1 antibody from 1 to 6-months of age or from 3 to 6-months of age clearly reduced DNA damage in the cerebral cortices of the 5×FAD mice to the level of normal mice at 6 months of age (see FIGS. 5I and 5J).

As described above, it was revealed that administration of the anti-HMGB1 antibody improves the pathology and cognitive function of AD model mice, and further that the antibody therapy targeting HMGB1 is effective for Alzheimer's disease.

(Bi-directional Suppression of Polymerization Between HMGB1 and Aβ)

Next, it was investigated whether the effect of the anti-HMGB1 antibody on Alzheimer's disease was a direct effect on HMGB1 toxicity or indirect effect on the polymerization process of amyloid β (Aβ).

It was already reported that Aβ and HMGB1 interact with each other (see Takata, K. et al., BiochemBiophys Res Commun 301, 699-703 (2003) and Takata, K. et al., Int J Alzheimers Dis 2012, 685739 (2012)). However, the influence of HMGB1 on Aβ such as the polymerization process of Aβ, the ratio of monomer/oligomer/polymer in Aβ, and the like have not been clarified yet. This point was analyzed.

First, conditions for evaluating the influence on HMGB1 in the process of aggregation of the $A\beta_{1-42}$ peptide were investigated. As a result, although not shown in the diagrams, we found that incubation at 37° C. for 48 hours is appropriated as conditions for detecting the aggregation in the Western blot and electron microscope as reported in Hortschansky, P. et al., Protein Sci 14, 1753-1759 (2005). and Guan, Y. et al., ACS Chem Neurosci 6, 1503-1508 (2015).

Next, it was investigated how HMGB1 influences the aggregation process of Aβ under the conditions. Specifically, various Aβ species such as monomers, oligomers (dimers to tetramers), ADDLs/protofibrils, and fibrils (see Haass, C. & Selkoe, D. J., Nat Rev Mol Cell Biol 8, 101-112 (2007) and Lambert, M P. et al., Proc Natl Acad Sci USA 95, 6448-6453 (1998)) were evaluated.

Figure 7A:
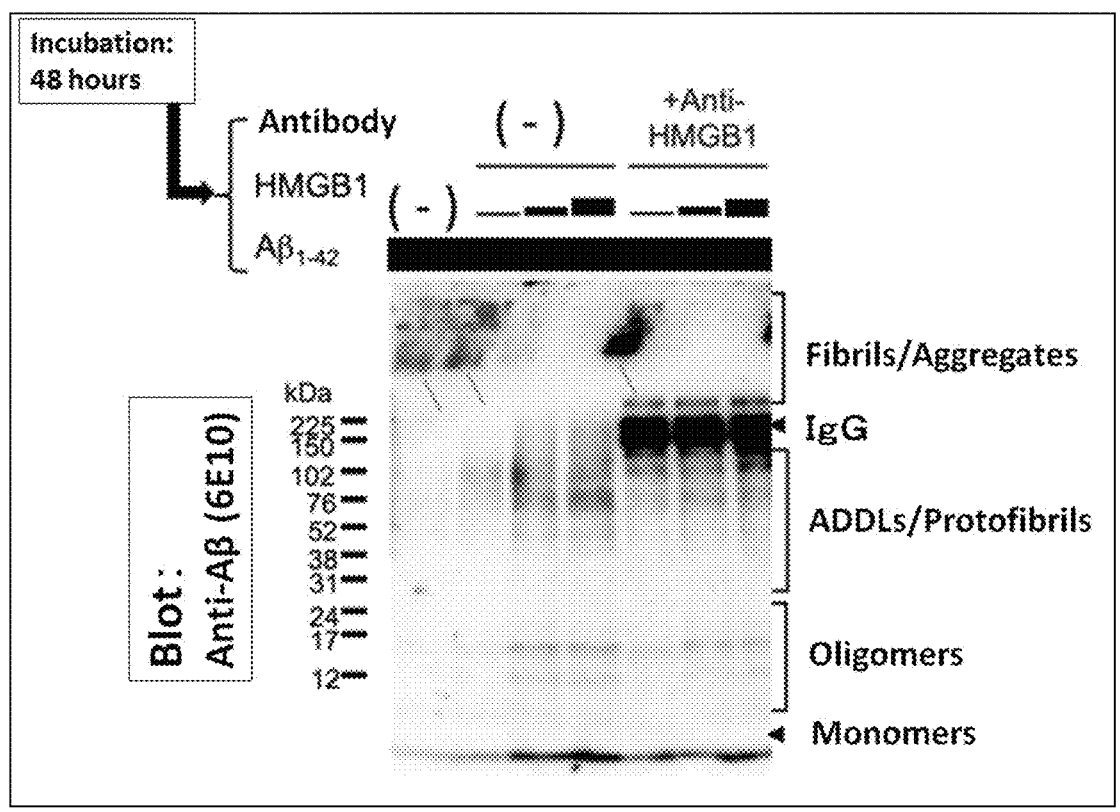
FIG. 7A is a photograph showing the result of analyzing the in vitro effects of HMGB1 and anti-HMGB1 antibody on amyloid β (AM polymerization, Aβ oligomerization, Aβ-HMGB1 heteromer formation, and HMGB1 oligomerization with the Western blot using the anti-Aβ antibody. Note that the samples were prepared by incubation at 37° C. for 48 hours. The gel made of 0.036% SDS was used. In addition, in the figure, "antibody (−)" shows the result of adding normal mouse IgG as control relative to the addition of the anti-HMGB1 antibody.
Figure 7B:
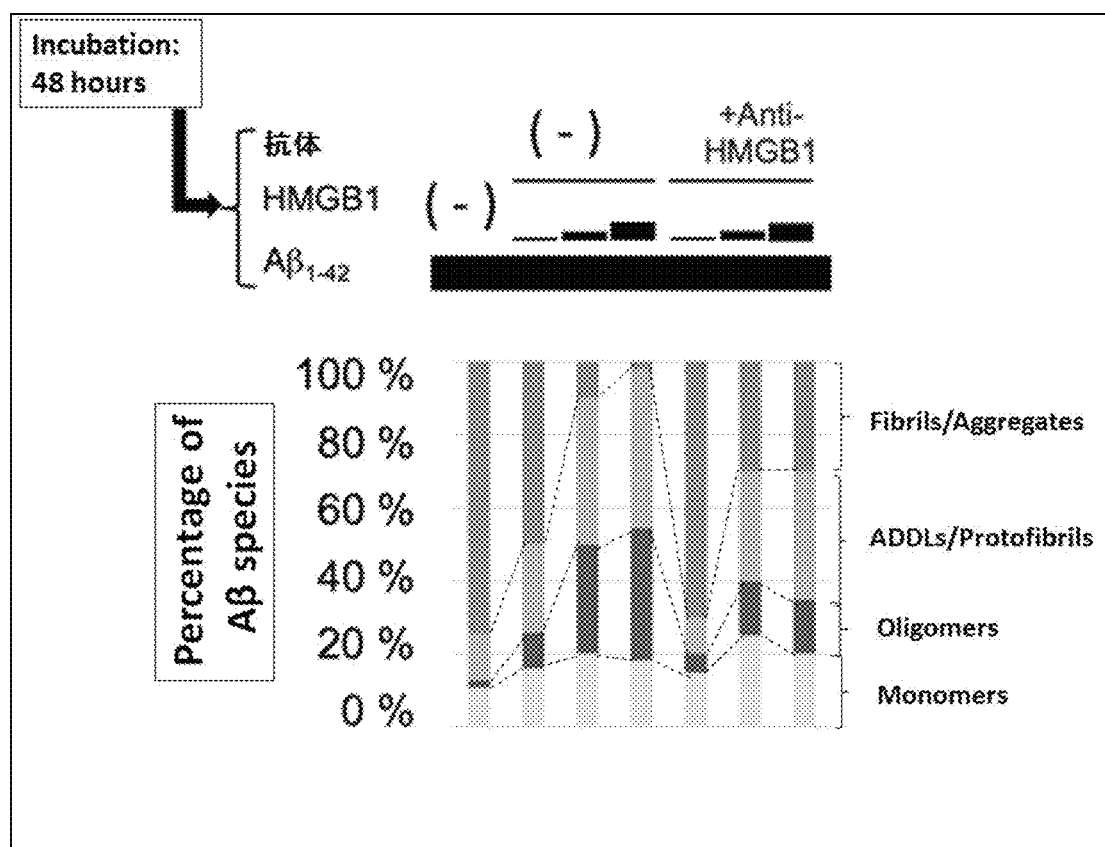
FIG. 7B is a cumulative bar chart showing the result of analyzing the in vitro effects of HMGB1 and anti-HMGB1 antibody on Aβ polymerization, Aβ oligomerization, Aβ-HMGB1 heteromer formation, and HMGB1 oligomerization with the Western blot using the anti-Aβ antibody (6E10). This figure shows the result of quantitatively analyzing the ratios among four types of Aβ species in the total Western blot signals of Aβ (IgG signals were excluded) shown in FIG. 7A. This figure also shows average values of experiments conducted three times.

As a result, as shown in FIG. 7A, the Western blot analysis revealed that HMGB1 clearly suppressed the Aβ polymerization and increased the ratios of oligomers and ADDLs among all Aβ species. It was also revealed that the addition of the anti-HMGB1 antibody to the samples suppressed increases of Aβ oligomers/ADDLs by the HMGB1 but increased the Aβ aggregates. These effects were not observed in the IgG control. In addition, as shown in FIG. 7B, the results of quantitative analysis supported the above-described findings.

Figure 7C:
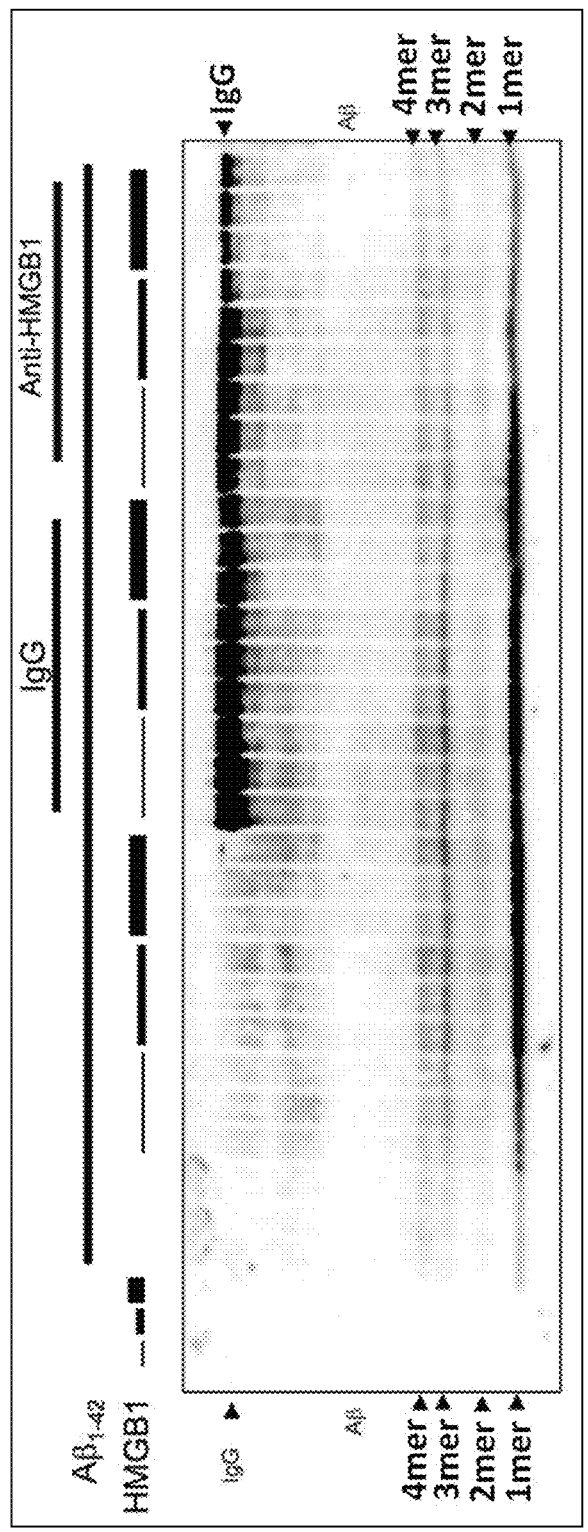
FIG. 7C is a photograph showing the result of further analyzing the effect of HMGB1 and anti-HMGB1 antibody on Aβ oligomerization with the Western blot using the anti-Aβ antibody (6E10). As shown in this figure, the monomers, oligomers and ADDLs/protofibrils of Aβ were increased in a HMGB1 dose-dependent manner. In addition, the anti-HMGB1 antibody inhibited the effect of HMGB1 on Aβ oligomerization. However, no inhibitory effect was observed with the addition of control IgG.

Next, focusing on Aβ species other than fibrils/aggregates, the experiments were repeated and revealed that the anti-HMGB1 antibody suppressed the increase of the Aβ monomers and oligomers/ADDLs by HMGB1 as shown in FIG. 7C.

Figure 7D:
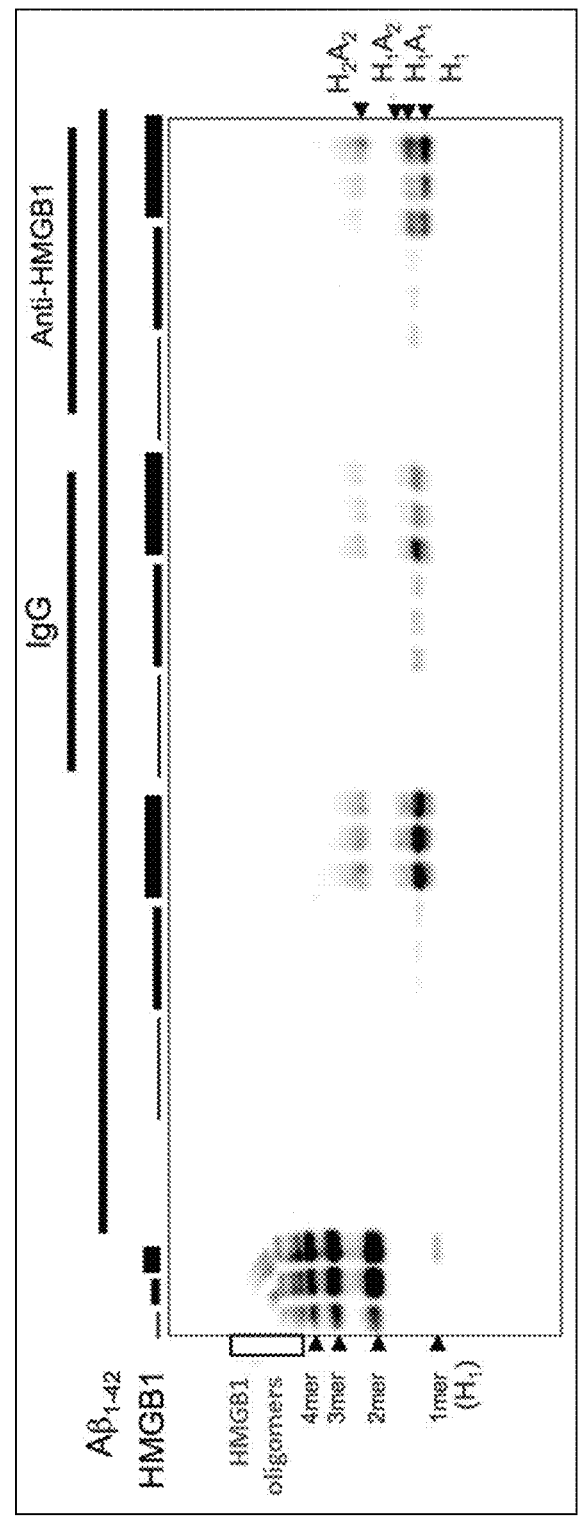
FIG. 7D is a photograph showing the result of analyzing in vitro polymerization of HMGB1 with the Western blot using the anti-HMGB1 antibody (rabbit-derived polyclonal antibody). The same samples as those shown in FIG. 7C were used.
Figure 7E:
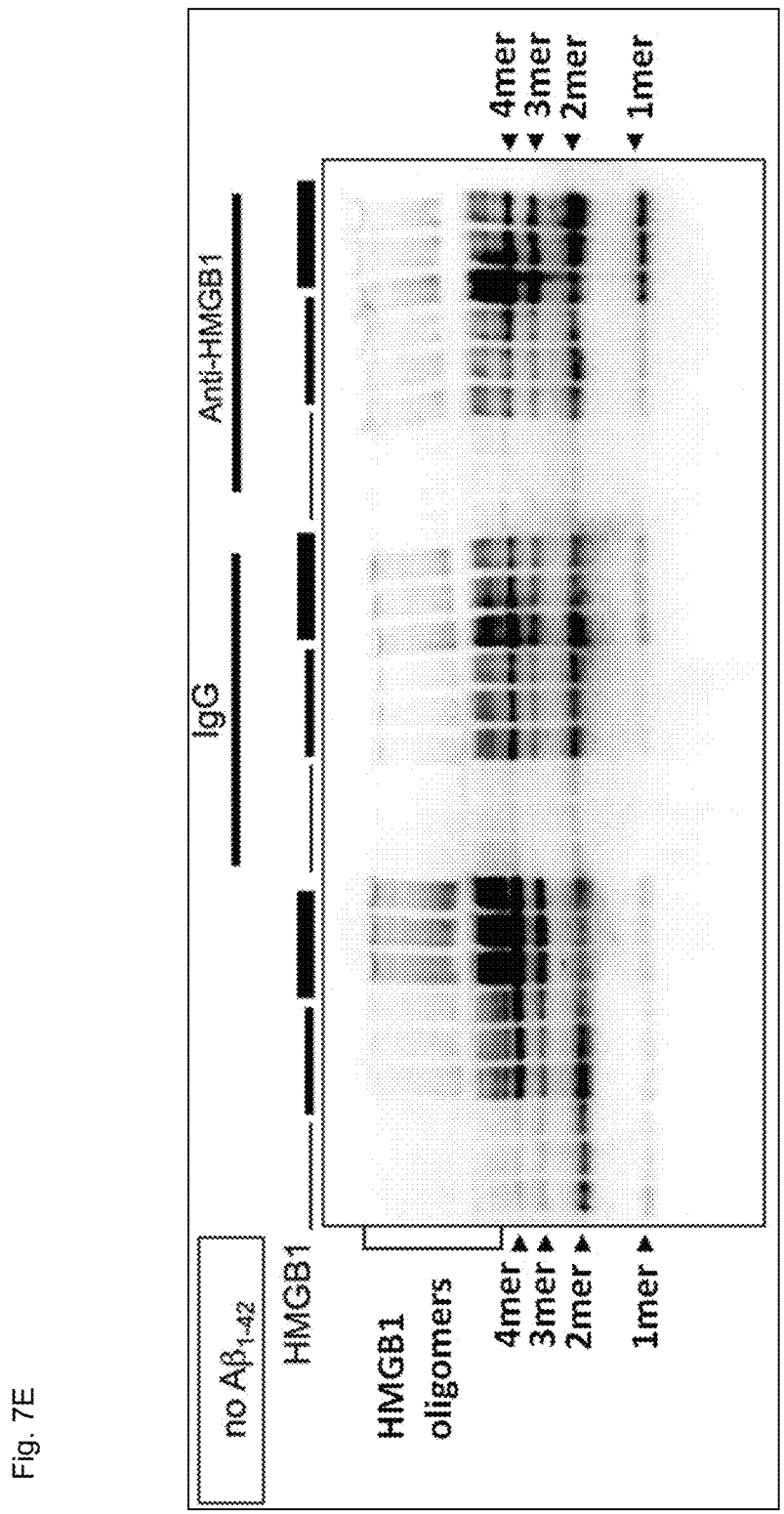
FIG. 7E is a photograph showing the result of analyzing in vitro polymerization of HMGB1 in the absence of Aβ with the Western blot using the anti-HMGB1 antibody (rabbit-derived polyclonal antibody). As shown in this figure, in the absence of Aβ, HMGB1 aggregation was promoted in a dose-dependent manner. The anti-HMGB1 antibody inhibited HMGB1 polymerization and increased the ratio of HMGB1 monomers and dimers. This effect was not observed with the control IgG.

On the other hand, as shown in FIG. 7D, it was revealed that the in vitro polymerization of HMGB1 is inhibited by the addition of A. Moreover, it was found that the mixture of Aβ and HMGB1 produced three bands corresponding to heterocomplexes of the Aβ and HMGB1. Based on the molecular weight, these heterocomplexes were expected to be H1A1 (HMGB1:Aβ=1:1) heterodimers, H1A2 (HMGB1:Aβ=1:2) heterodimers, and H2A2 (HMGB1:Aβ=2:2) heterodimers (see D in FIG. 7). In addition, a commercially-available anti-HMGB1 polyclonal antibody recognized these Aβ-HMGB1 heterocomplexes, and the Western blot also revealed that the anti-HMGB1 monoclonal antibody (2C8C antibody) affected the formation of these heterocomplexes. That is, it was revealed that the addition of the anti-HMGB1 monoclonal antibody increased the HMGB1 monomer (H1) and reduced H2A2. Moreover, as shown in FIG. 7E, it was also confirmed that the anti-HMGB1 monoclonal antibody suppressed polymerization of only HMGB1 and increased the HMGB1 monomers. It should be noted that an extremely high molecular weight substance reminiscent of fibril was not found in the pure incubation of HMGB1.

Figure 7F:
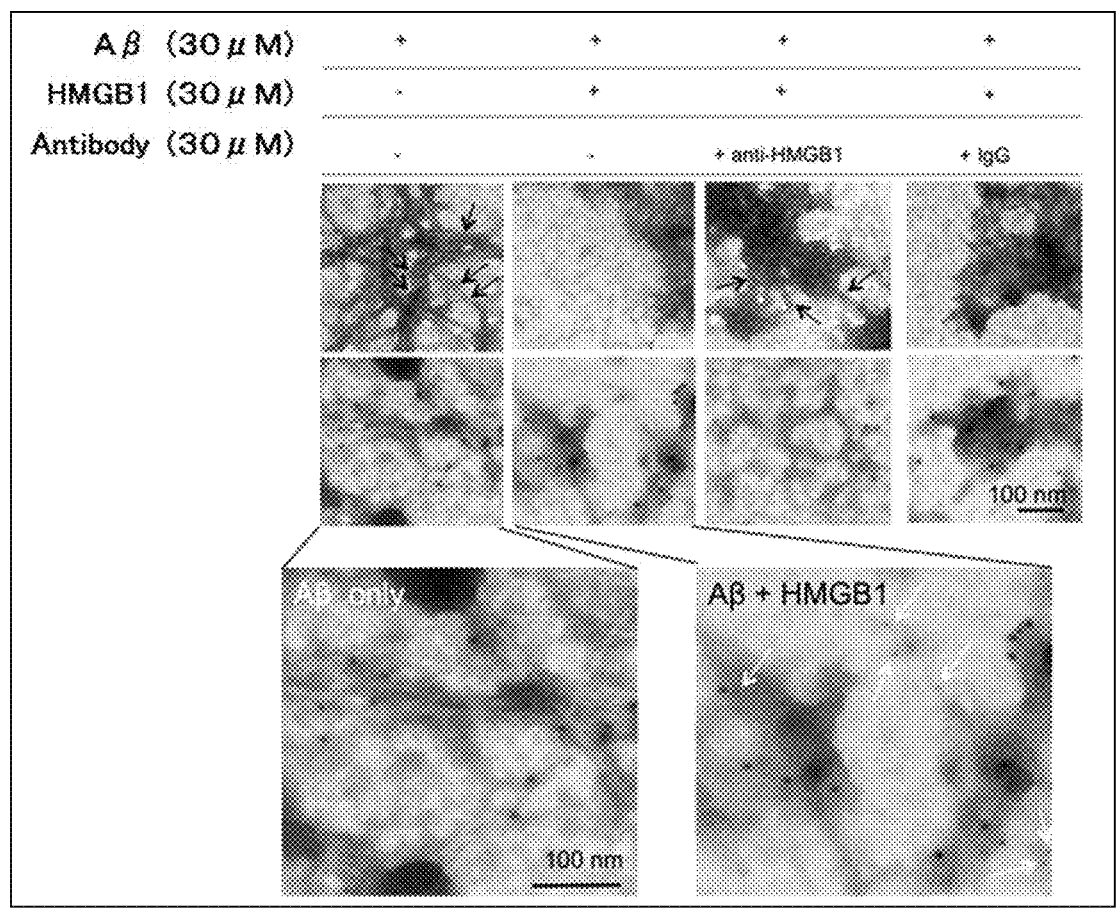
FIG. 7F is a photograph showing the result of observing in vitro aggregation samples with an electron microscope. As shown in this figure, HMGB1 inhibited fibril formation of Aβ (indicated by the black arrows) and increased amorphous structures that might correspond to Aβ oligomers or ADDLs/protofibrils. On the other hand, the addition of the anti-HMGB1 antibody recovered the fibril formation (indicated by the black arrows). From the result of analysis using an immunoelectron microscope, HMGB1 was located in the periphery of the Aβ-fibrils (indicated by the white arrows), presumably inhibiting extension of the Aβ-fibrils.

Next, the effect of HMGB1 on Aβ polymerization was analyzed by electron microscopy. As a result, as shown in FIG. 7F, it was found that HMGB1 inhibited the formation of Aβ-fibril, and on the other hand, the anti-HMGB1 monoclonal antibody recovered the formation of Aβ-fibril.

These results collectively indicate that Aβ and HMGB1 mutually inhibit polymerization of their molecules. As a result of the mutual interference, HMGB1 inhibited the formation of fibril of Aβ and increased the oligomer and protofibril of Aβ (see FIG. 7A). On the other hand, the anti-HMGB1 antibody inhibited polymerization of both Aβ and HMGB1, and in the case of Aβ polymerization, reduced the Aβ oligomer and protofibril in the presence of HMGB1 (see FIGS. 7A to 7C). Although not shown in the diagrams, the Western blot analysis did not show fibrils of HMGB1.

(Influence of Anti-HMGB1 Antibody on Phagocytosis of Microglia)

The Aβ-HMGB1 complex has been reported to be likely to be phagocytized by the microglia (see Takata, K. et al., Int J Alzheimers Dis 2012, 685739 (2012)). In view of this, the influence of the anti-HMGB1 antibody on the Aβ phagocytosis by the microglia was analyzed.

Figure 8A:
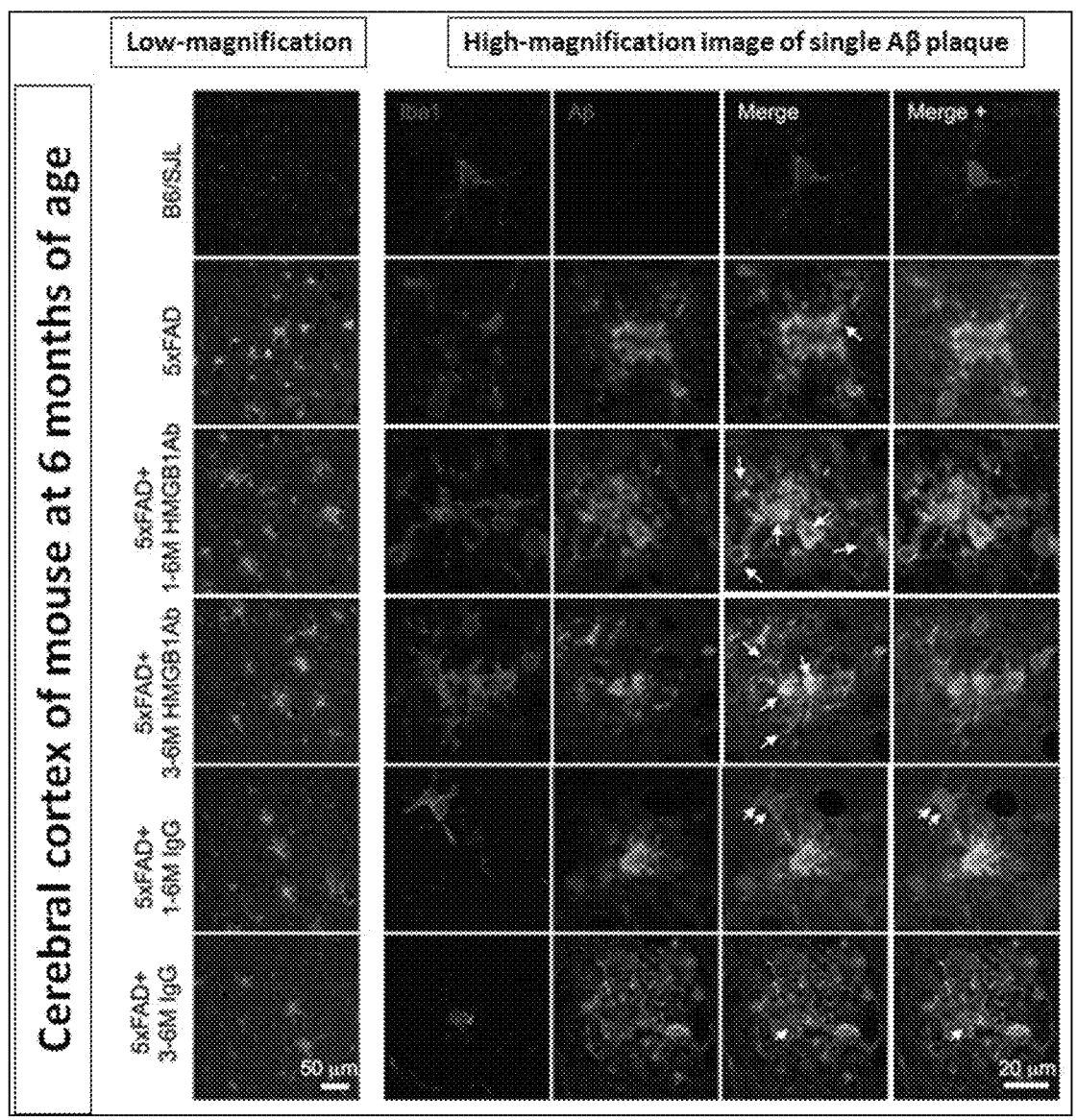
FIG. 8A is fluorescence microscope photographs showing the result of analyzing the in vivo effect of the anti-HMGB1 monoclonal antibody on microglia in 5×FAD mice. In this figure, the result of low-magnification observation of the cerebral cortex (RSD) and the result of high-magnification observation of a representative Aβ plaque of 5×FAD mice (at 6 months of age) are shown. As a result, after treatment with the anti-HMGB1 antibody (1 to 6-months and 3 to 6-months treatment groups), a large number of microglia formed Aβ plaques, and the microglia incorporated Aβ into the cytoplasm.
Figure 8B:
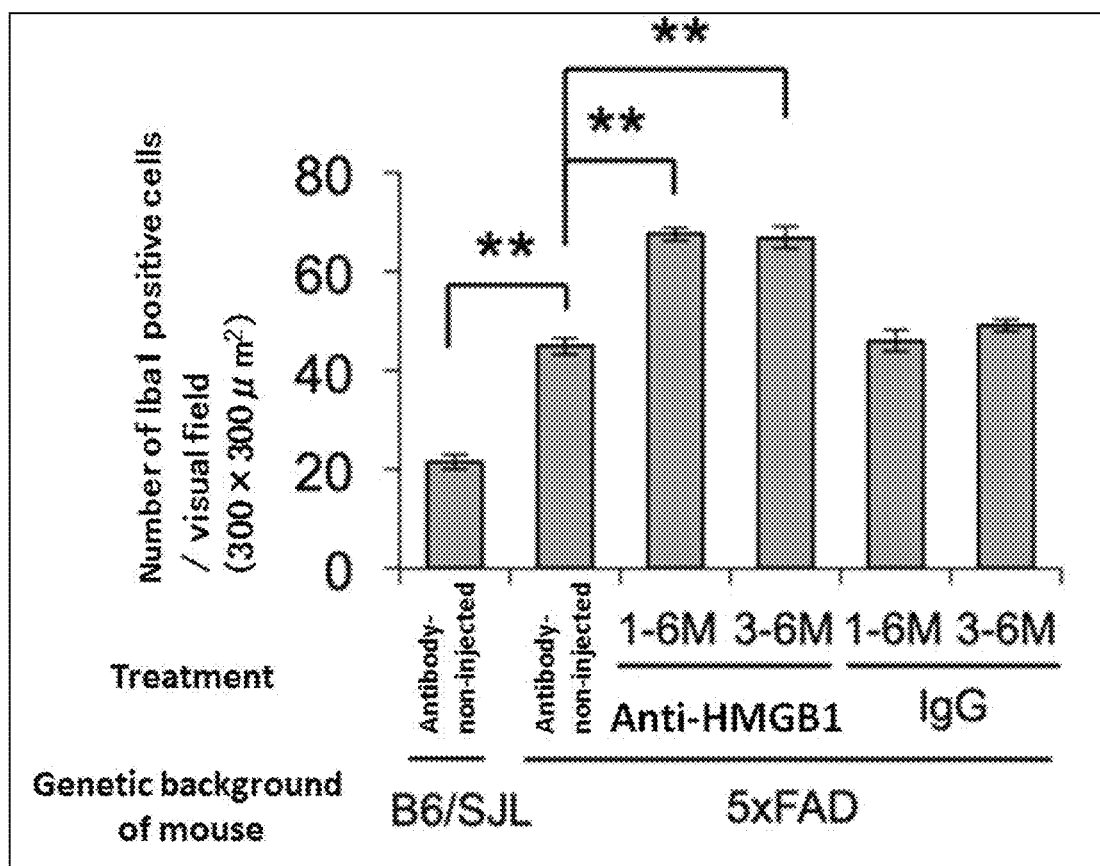
FIG. 8B is a graph showing the result of quantitatively analyzing the number of microglia in a visual field (n=10, cerebral cortex) of the fluorescence microscope photograph shown in FIG. 8A. As shown in this figure, it was confirmed that the number of microglia in a visual field was increased in the mice after the treatment with the anti-HMGB1 antibody.
Figure 8C:
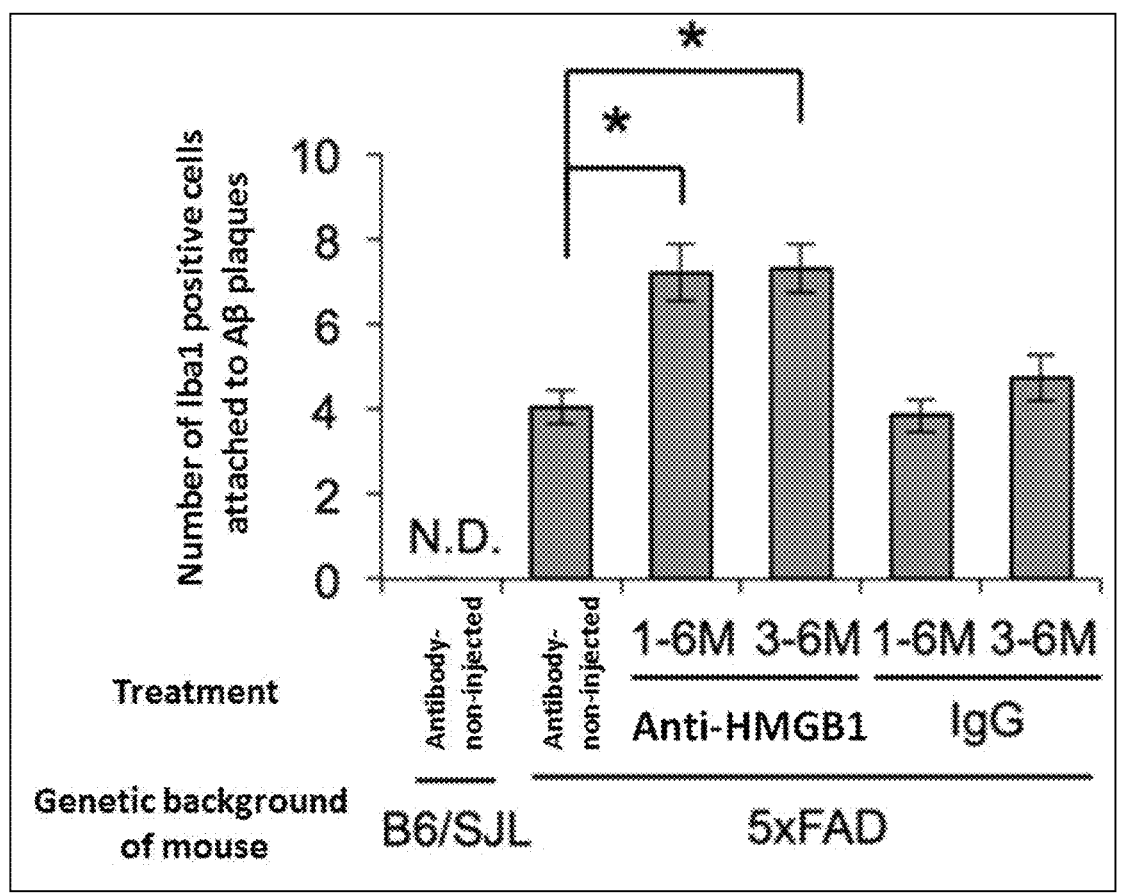
FIG. 8C is a graph showing the result of quantitatively analyzing the number of microglia forming plaques in a visual field (n=30, cerebral cortex) of the fluorescence microscope photograph shown in FIG. 8A. As shown in this figure, it was confirmed that the number of microglia forming plaques was increased in the mice after the treatment with the anti-HMGB1 antibody.

As a result, as shown in FIGS. 8A to 8C, it was confirmed from the immunohistochemical analysis on the microglia-specific marker Ibal that the injection of the anti-HMGB1 antibody (2C8C antibody) increased the number of microglia. Particularly, it was revealed that around Aβ aggregates, these microglia incorporated Aβ into the cytoplasm and the anti-HMGB1 antibody enhanced the phagocytosis of the Aβ/HMGB1 complex.

Figure 8D:
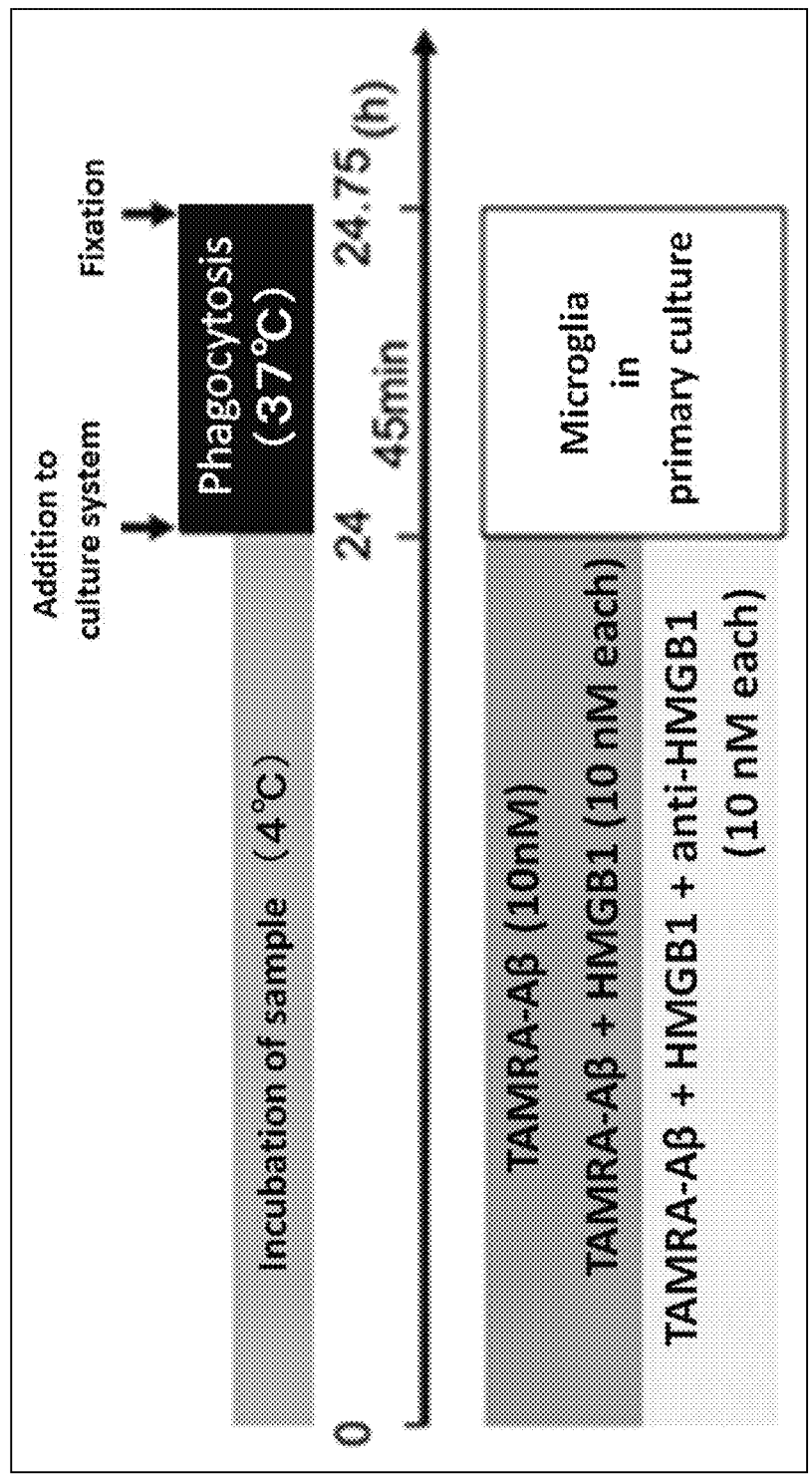
FIG. 8D is a diagram schematically showing the protocol for detecting phagocytosis of fluorescent (TAMRA-)Aβ by rat microglia in primarily cultures. As shown in this figure, TAMRA-Aβ, human HMGB1, and anti-HMGB1 antibodies were mixed, pre-incubated, and added to the microglia in the primary culture.
Figure 8E:
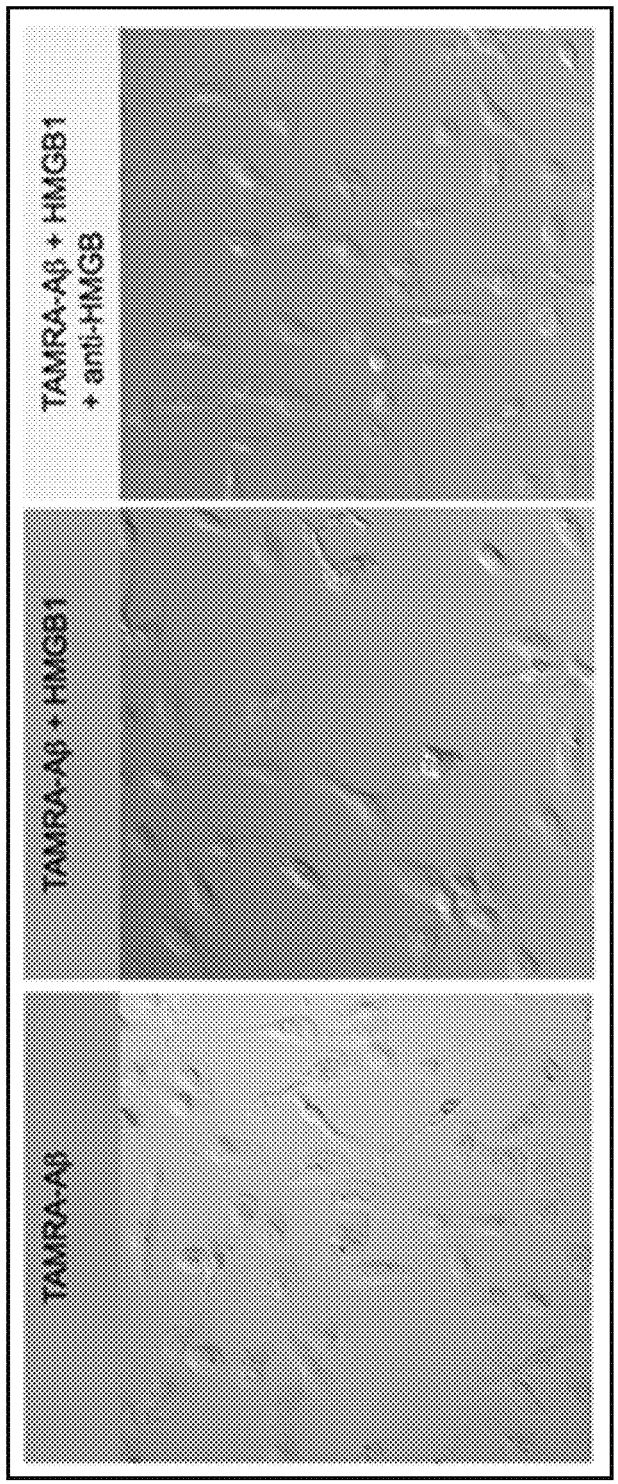
FIG. 8E is a photograph showing the result of detecting phagocytosis of fluorescent Aβ by the rat microglia in primarily cultures.
Figure 8F:
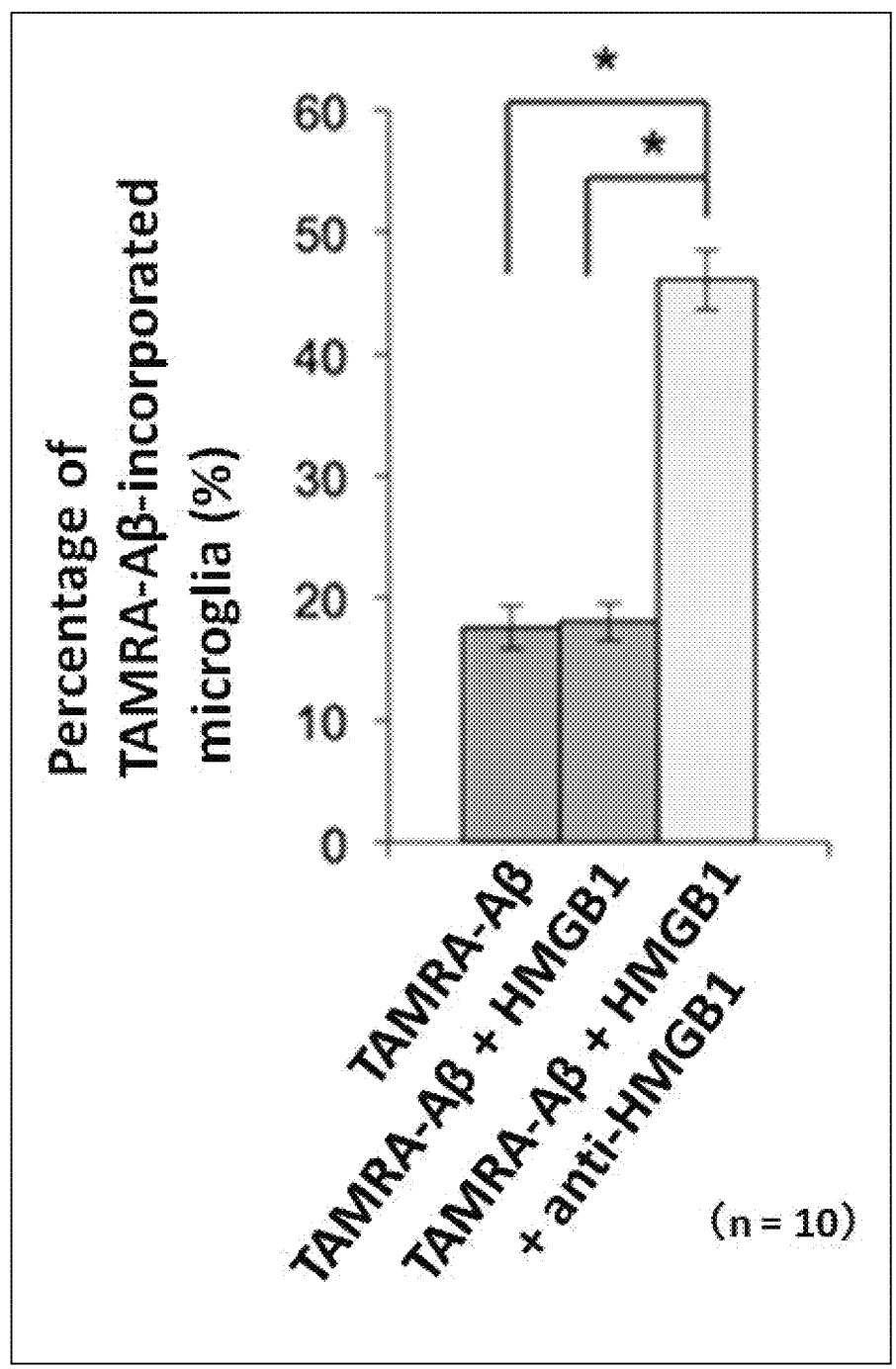
FIG. 8F is a graph showing the result of quantitatively analyzing the phagocytosis of the fluorescent Aβ by the rat microglia in primarily cultures.

In addition, as shown in FIG. 8D to F, microglia phagocytosis of the Aβ HMGB1/anti-HMGB1 antibody complex was higher than that of Aβ or Aβ-HMGB1 complex in a microglial primary culture.

These results suggest that the decrease of the Aβ deposition by the anti-HMGB1 antibody is not due to the direct effect of HMGB1 in the Aβ polymerization but resulted from enhanced Aβ phagocytosis of the Aβ/HMGB1/anti-HMGB1 antibody complex by microglia. Presumably this occurred through Fc receptor-mediated phagocytosis as in the case of the Aβ antibody described in Bard, F. et al., Nat Med 6, 916-919 (2000).

INDUSTRIAL APPLICABILITY

As described above, since the antibody of the present invention has a high affinity for the HMGB1 protein and is capable of recovering various lesions of Alzheimer's disease, the antibody of the present invention is useful particularly in treating or preventing this disease.

SEQUENCE LISTING FREE TEXT

SEQ ID NO: 1
<223> Signal Sequence, Variable Region, and Constant Region of Light Chain of 2C8C
SEQ ID NO: 3
<223> Light Chain Variable Region of 2C8C
SEQ ID NO: 4
<223> CDR1 of Light Chain of 2C8C
SEQ ID NO: 5
<223> CDR2 of Light Chain of 2C8C
SEQ ID NO: 6
<223> CDR3 of Light Chain of 2C8C
SEQ ID NO: 7
<223> Signal Sequence, Variable Region, and Constant Region of Heavy Chain of 2C8C
SEQ ID NO: 9
<223> Heavy Chain Variable Region of 2C8C
SEQ ID NO: 10
<223> CDR1 of Heavy Chain of 2C8C
SEQ ID NO: 11
<223> CDR2 of Heavy Chain of 2C8C
SEQ ID NO: 12
<223> CDR3 of Heavy Chain of 2C8C
SEQ ID NO: 13
<223> GeneRacer 5' Primer
SEQ ID NO: 14
<223> mIgG2a 3' Primer
SEQ ID NO: 15
<223> mIgk 3' Primer

The invention claimed is:

1. A monoclonal antibody against HMGB1 (High Mobility Group Box 1), the antibody having any one of the following features (a) and (b):
   (a) comprising
      a light chain variable region comprising complementarity-determining regions 1-3 as defined by amino acid sequences of SEQ ID NOs: 4 to 6 respectively, and
      a heavy chain variable region comprising complementarity-determining regions 1-3 as defined by amino acid sequences of SEQ ID NOs: 10 to 12 respectively; and
   (b) comprising
      a light chain variable region comprising an amino acid sequence of SEQ ID NO: 3 or the amino acid sequence of SEQ ID NO: 3 in which 1 to 10 amino acids in the framework region are substituted, deleted, added, and/or inserted, and
      a heavy chain variable region comprising an amino acid sequence of SEQ ID NO: 9 or the amino acid sequence of SEQ ID NO: 9 in which 1 to 10 amino acids in the framework region are substituted, deleted, added, and/or inserted.

2. A composition comprising the antibody according to claim 1, and further comprising a pharmaceutically acceptable carrier or medium.

3. A DNA encoding the antibody according to claim 1.

4. A vector comprising the DNA according to claim 3.

5. A host cell producing the antibody according to claim 1.

6. A hybridoma producing the antibody according to claim 1.

7. A host cell comprising the DNA according to claim 3.

8. A host cell comprising the DNA according the vector according to claim 4.

\* \* \* \* \*

```
                        SEQUENCE LISTING

<160> NUMBER OF SEQ ID NOS: 15

<210> SEQ ID NO 1
<211> LENGTH: 717
<212> TYPE: DNA
<213> ORGANISM: Mus musculus
<220> FEATURE:
<221> NAME/KEY: CDS
<222> LOCATION: (1)..(702)
<223> OTHER INFORMATION: Signal peptide, Variable Region and Constant
      Region of Light Chain (2C8C)

<400> SEQUENCE: 1 atg gtt ttc aca cct cag ata ctt gga ctt atg ctt ttt tgg att tca        48
Met Val Phe Thr Pro Gln Ile Leu Gly Leu Met Leu Phe Trp Ile Ser
1               5                  10                  15 gcc tcc aga ggt gat att gtg cta act cag tct cca gcc acc ctg tct        96
Ala Ser Arg Gly Asp Ile Val Leu Thr Gln Ser Pro Ala Thr Leu Ser
            20                  25                  30 gtg act cca gga gat agc gtc agt ctt tcc tgc agg gcc agc caa agt       144
Val Thr Pro Gly Asp Ser Val Ser Leu Ser Cys Arg Ala Ser Gln Ser
        35                  40                  45 att agc aac aac cta cac tgg tat caa caa aaa tca cat gag tct cca       192
Ile Ser Asn Asn Leu His Trp Tyr Gln Gln Lys Ser His Glu Ser Pro
    50                  55                  60 agg ctt ctc atc aag tat gct tcc cag tcc atc tct ggg atc ccc tcc       240
Arg Leu Leu Ile Lys Tyr Ala Ser Gln Ser Ile Ser Gly Ile Pro Ser
65                  70                  75                  80 agg ttc agt ggc agt gga tca ggg aca gat ttc act ctc agt atc aac       288
Arg Phe Ser Gly Ser Gly Ser Gly Thr Asp Phe Thr Leu Ser Ile Asn
                85                  90                  95 agt gtg gag act gaa gat ttt gga atg tat ttc tgt caa cag act aac       336
Ser Val Glu Thr Glu Asp Phe Gly Met Tyr Phe Cys Gln Gln Thr Asn
```

```
             100                 105                 110
agc tgg ccg ctc acg ttc ggt gct ggg acc aag ctg gag ctg aaa cgg       384
Ser Trp Pro Leu Thr Phe Gly Ala Gly Thr Lys Leu Glu Leu Lys Arg
        115                 120                 125 gct gat gct gca cca act gta tcc atc ttc cca cca tcc agt gag cag       432
Ala Asp Ala Ala Pro Thr Val Ser Ile Phe Pro Pro Ser Ser Glu Gln
130                 135                 140 tta aca tct gga ggt gcc tca gtc gtg tgc ttc ttg aac aac ttc tac       480
Leu Thr Ser Gly Gly Ala Ser Val Val Cys Phe Leu Asn Asn Phe Tyr
145                 150                 155                 160 ccc aaa gac atc aat gtc aag tgg aag att gat ggc agt gaa cga caa       528
Pro Lys Asp Ile Asn Val Lys Trp Lys Ile Asp Gly Ser Glu Arg Gln
                165                 170                 175 aat ggc gtc ctg aac agt tgg act gat cag gac agc aaa gac agc acc       576
Asn Gly Val Leu Asn Ser Trp Thr Asp Gln Asp Ser Lys Asp Ser Thr
            180                 185                 190 tac agc atg agc agc acc ctc acg ttg acc aag gac gag tat gaa cga       624
Tyr Ser Met Ser Ser Thr Leu Thr Leu Thr Lys Asp Glu Tyr Glu Arg
        195                 200                 205 cat aac agc tat acc tgt gag gcc act cac aag aca tca act tca ccc       672
His Asn Ser Tyr Thr Cys Glu Ala Thr His Lys Thr Ser Thr Ser Pro
    210                 215                 220 att gtc aag agc ttc aac agg aat gag tgt tagttaatta agcgg            717
Ile Val Lys Ser Phe Asn Arg Asn Glu Cys
225                 230

<210> SEQ ID NO 2
<211> LENGTH: 234
<212> TYPE: PRT
<213> ORGANISM: Mus musculus

<400> SEQUENCE: 2

Met Val Phe Thr Pro Gln Ile Leu Gly Leu Met Leu Phe Trp Ile Ser
1               5                   10                  15

Ala Ser Arg Gly Asp Ile Val Leu Thr Gln Ser Pro Ala Thr Leu Ser
            20                  25                  30

Val Thr Pro Gly Asp Ser Val Ser Leu Ser Cys Arg Ala Ser Gln Ser
        35                  40                  45

Ile Ser Asn Asn Leu His Trp Tyr Gln Gln Lys Ser His Glu Ser Pro
    50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Thr Glu Asp Phe Gly Met Tyr Phe Cys Gln Gln Thr Asn
            100                 105                 110

Ser Trp Pro Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
```

```
                195                 200                 205
His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 3
<211> LENGTH: 107
<212> TYPE: PRT
<213> ORGANISM: Mus musculus
<220> FEATURE:
<221> NAME/KEY: SITE
<222> LOCATION: (1)..(107)
<223> OTHER INFORMATION: Variable Region of Light Chain (2C8C)

<400> SEQUENCE: 3

```
Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Thr Asn Ser Trp Pro Leu
                85                  90                  95

Thr Phe Gly Ala Gly Thr Lys Leu Glu Leu Lys
                100                 105
```

<210> SEQ ID NO 4
<211> LENGTH: 11
<212> TYPE: PRT
<213> ORGANISM: Mus musculus
<220> FEATURE:
<221> NAME/KEY: SITE
<222> LOCATION: (1)..(11)
<223> OTHER INFORMATION: CDR1 of Light Chain (2C8C)

<400> SEQUENCE: 4

```
Arg Ala Ser Gln Ser Ile Ser Asn Asn Leu His
1               5                   10
```

<210> SEQ ID NO 5
<211> LENGTH: 8
<212> TYPE: PRT
<213> ORGANISM: Mus musculus
<220> FEATURE:
<221> NAME/KEY: SITE
<222> LOCATION: (1)..(8)
<223> OTHER INFORMATION: CDR2 of Light Chain (2C8C)

<400> SEQUENCE: 5

```
Tyr Ala Ser Gln Ser Ile Ser Gly
1               5
```

<210> SEQ ID NO 6
<211> LENGTH: 9
<212> TYPE: PRT
<213> ORGANISM: Mus musculus
<220> FEATURE:
<221> NAME/KEY: SITE
<222> LOCATION: (1)..(9)

<223> OTHER INFORMATION: CDR3 of Light Chain (2C8C)

<400> SEQUENCE: 6

Gln Gln Thr Asn Ser Trp Pro Leu Thr
1               5

<210> SEQ ID NO 7
<211> LENGTH: 711
<212> TYPE: DNA
<213> ORGANISM: Mus musculus
<220> FEATURE:
<221> NAME/KEY: CDS
<222> LOCATION: (1)..(711)
<223> OTHER INFORMATION: Signal peptide, Variable Region and Constant
      Region of Heavy Chain (2C8C)

<400> SEQUENCE: 7

```
atg aca ctg act cta acc atg gga tgg agc tgg atc ttt ctc ttc ctc        48
Met Thr Leu Thr Leu Thr Met Gly Trp Ser Trp Ile Phe Leu Phe Leu
1               5                   10                  15 ctg tca gga act gca ggt gtc cat tgc cag gtc cag ctg cag cag tct        96
Leu Ser Gly Thr Ala Gly Val His Cys Gln Val Gln Leu Gln Gln Ser
            20                  25                  30 gga cct gag ctg gtg aag cct gga gct tca gtg aag ctg tcc tgc aag       144
Gly Pro Glu Leu Val Lys Pro Gly Ala Ser Val Lys Leu Ser Cys Lys
        35                  40                  45 gct tct ggc tac acc ttc act gac tat act ata cac tgg gtg aag cag       192
Ala Ser Gly Tyr Thr Phe Thr Asp Tyr Thr Ile His Trp Val Lys Gln
    50                  55                  60 agt cct gga cag gga ctt gag tgg att gga tgg att tat cct gga agt       240
Ser Pro Gly Gln Gly Leu Glu Trp Ile Gly Trp Ile Tyr Pro Gly Ser
65                  70                  75                  80 ggt aat act aag tac aat gac aag ttc aag ggc aag gcc aca atg act       288
Gly Asn Thr Lys Tyr Asn Asp Lys Phe Lys Gly Lys Ala Thr Met Thr
                85                  90                  95 gca gac aaa tcc tcc agc aca gcc tac atg cag ctc agc agc ctg acc       336
Ala Asp Lys Ser Ser Ser Thr Ala Tyr Met Gln Leu Ser Ser Leu Thr
            100                 105                 110 tct gag gat tct gcg gtc tat ttc tgt gca aga ggg ttt gct tac tgg       384
Ser Glu Asp Ser Ala Val Tyr Phe Cys Ala Arg Gly Phe Ala Tyr Trp
        115                 120                 125 ggc caa ggg act ctg gtc act gtc tct gca gcc aaa aca aca gcc cca       432
Gly Gln Gly Thr Leu Val Thr Val Ser Ala Ala Lys Thr Thr Ala Pro
    130                 135                 140 tcg gtc tat cca ctg gcc cct gtg tgt gga gat aca agt ggc tcc tcg       480
Ser Val Tyr Pro Leu Ala Pro Val Cys Gly Asp Thr Ser Gly Ser Ser
145                 150                 155                 160 gtg act cta gga tgc ctg gtc aag ggt tat ttc cct gag cca gtg acc       528
Val Thr Leu Gly Cys Leu Val Lys Gly Tyr Phe Pro Glu Pro Val Thr
                165                 170                 175 ttg acc tgg aac tct gga tcc ctg tcc agt ggt gtg cac acc ttc cca       576
Leu Thr Trp Asn Ser Gly Ser Leu Ser Ser Gly Val His Thr Phe Pro
            180                 185                 190 gct gtc ctg cag tct gac ctc tac acc ctc agc agc tca gtg act gta       624
Ala Val Leu Gln Ser Asp Leu Tyr Thr Leu Ser Ser Ser Val Thr Val
        195                 200                 205 acc tcg agc acc tgg ccc agc cag tcc atc acc tgc aat gtg gcc cac       672
Thr Ser Ser Thr Trp Pro Ser Gln Ser Ile Thr Cys Asn Val Ala His
    210                 215                 220 ccg gca agc agc acc aag gtg gac aag aaa att gga tcc                   711
Pro Ala Ser Ser Thr Lys Val Asp Lys Lys Ile Gly Ser
225                 230                 235
```

<210> SEQ ID NO 8
<211> LENGTH: 237
<212> TYPE: PRT
<213> ORGANISM: Mus musculus

<400> SEQUENCE: 8

Met Thr Leu Thr Leu Thr Met Gly Trp Ser Trp Ile Phe Leu Phe Leu
1               5                   10                  15

Leu Ser Gly Thr Ala Gly Val His Cys Gln Val Gln Leu Gln Gln Ser
            20                  25                  30

Gly Pro Glu Leu Val Lys Pro Gly Ala Ser Val Lys Leu Ser Cys Lys
        35                  40                  45

Ala Ser Gly Tyr Thr Phe Thr Asp Tyr Thr Ile His Trp Val Lys Gln
    50                  55                  60

Ser Pro Gly Gln Gly Leu Glu Trp Ile Gly Trp Ile Tyr Pro Gly Ser
65                  70                  75                  80

Gly Asn Thr Lys Tyr Asn Asp Lys Phe Lys Gly Lys Ala Thr Met Thr
                85                  90                  95

Ala Asp Lys Ser Ser Ser Thr Ala Tyr Met Gln Leu Ser Ser Leu Thr
            100                 105                 110

Ser Glu Asp Ser Ala Val Tyr Phe Cys Ala Arg Gly Phe Ala Tyr Trp
        115                 120                 125

Gly Gln Gly Thr Leu Val Thr Val Ser Ala Ala Lys Thr Thr Ala Pro
    130                 135                 140

Ser Val Tyr Pro Leu Ala Pro Val Cys Gly Asp Thr Ser Gly Ser Ser
145                 150                 155                 160

Val Thr Leu Gly Cys Leu Val Lys Gly Tyr Phe Pro Glu Pro Val Thr
                165                 170                 175

Leu Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Thr Ser Ser Thr Trp Pro Ser Gln Ser Ile Thr Cys Asn Val Ala His
    210                 215                 220

Pro Ala Ser Ser Thr Lys Val Asp Lys Lys Ile Gly Ser
225                 230                 235

<210> SEQ ID NO 9
<211> LENGTH: 113
<212> TYPE: PRT
<213> ORGANISM: Mus musculus
<220> FEATURE:
<221> NAME/KEY: SITE
<222> LOCATION: (1)..(113)
<223> OTHER INFORMATION: Variable Region of Heavy Chain (2C8C)

<400> SEQUENCE: 9

Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Thr Ile His Trp Val Lys Gln Ser Pro Gly Gln Gly Leu Glu Trp Ile
        35                  40                  45

Gly Trp Ile Tyr Pro Gly Ser Gly Asn Thr Lys Tyr Asn Asp Lys Phe
    50                  55                  60

Lys Gly Lys Ala Thr Met Thr Ala Asp Lys Ser Ser Ser Thr Ala Tyr

```
                65                  70                  75                  80
Met Gln Leu Ser Ser Leu Thr Ser Glu Asp Ser Ala Val Tyr Phe Cys
                    85                  90                  95
Ala Arg Gly Phe Ala Tyr Trp Gly Gln Gly Thr Leu Val Thr Val Ser
                100                 105                 110

Ala

<210> SEQ ID NO 10
<211> LENGTH: 5
<212> TYPE: PRT
<213> ORGANISM: Mus musculus
<220> FEATURE:
<221> NAME/KEY: SITE
<222> LOCATION: (1)..(5)
<223> OTHER INFORMATION: CDR1 of Heavy Chain (2C8C)

<400> SEQUENCE: 10

Asp Tyr Thr Ile His
1               5

<210> SEQ ID NO 11
<211> LENGTH: 17
<212> TYPE: PRT
<213> ORGANISM: Mus musculus
<220> FEATURE:
<221> NAME/KEY: SITE
<222> LOCATION: (1)..(17)
<223> OTHER INFORMATION: CDR2 of Heavy Chain (2C8C)

<400> SEQUENCE: 11

Trp Ile Tyr Pro Gly Ser Gly Asn Thr Lys Tyr Asn Asp Lys Phe Lys
1               5                   10                  15

Gly

<210> SEQ ID NO 12
<211> LENGTH: 4
<212> TYPE: PRT
<213> ORGANISM: Mus musculus
<220> FEATURE:
<221> NAME/KEY: SITE
<222> LOCATION: (1)..(4)
<223> OTHER INFORMATION: CDR3 of Heavy Chain (2C8C)

<400> SEQUENCE: 12

Gly Phe Ala Tyr
1

<210> SEQ ID NO 13
<211> LENGTH: 23
<212> TYPE: DNA
<213> ORGANISM: Artificial Sequence
<220> FEATURE:
<223> OTHER INFORMATION: Synthetic sequence, GeneRacer 5'-primer

<400> SEQUENCE: 13
cgactggagc acgaggacac tga                                               23

<210> SEQ ID NO 14
<211> LENGTH: 28
<212> TYPE: DNA
<213> ORGANISM: Artificial Sequence
<220> FEATURE:
<223> OTHER INFORMATION: Synthetic sequence, mIgG2a 3'-primer

<400> SEQUENCE: 14
```

```
ggatccaatt ttcttgtcca ccttggtg                                              28

<210> SEQ ID NO 15
<211> LENGTH: 38
<212> TYPE: DNA
<213> ORGANISM: Artificial Sequence
<220> FEATURE:
<223> OTHER INFORMATION: Synthetic sequence, mIgk 3'-primer

<400> SEQUENCE: 15
ccgcttaatt aactaacact cattcctgtt gaagctct                                   38
```